US011192949B2

(12) United States Patent
Arts et al.

(10) Patent No.: US 11,192,949 B2
(45) Date of Patent: *Dec. 7, 2021

(54) HIV-1 VACCINE

(71) Applicant: CASE WESTERN RESERVE UNIVERSITY, Cleveland, OH (US)

(72) Inventors: Eric J. Arts, Cleveland, OH (US); Annette Burkhouse, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 518 days.

This patent is subject to a terminal disclaimer.

(21) Appl. No.: 16/000,695

(22) Filed: Jun. 5, 2018

(65) Prior Publication Data
US 2019/0127466 A1 May 2, 2019

Related U.S. Application Data

(63) Continuation of application No. 14/524,923, filed on Oct. 27, 2014, now Pat. No. 9,988,451.

(60) Provisional application No. 61/895,661, filed on Oct. 25, 2013.

(51) Int. Cl.
C07K 16/28 (2006.01)
A61K 39/12 (2006.01)
C07K 16/10 (2006.01)
A61K 39/00 (2006.01)

(52) U.S. Cl.
CPC .......... C07K 16/2812 (2013.01); A61K 39/12 (2013.01); C07K 16/1063 (2013.01); A61K 2039/5254 (2013.01); A61K 2039/575 (2013.01); C12N 2740/16122 (2013.01); C12N 2740/16134 (2013.01)

(58) Field of Classification Search
None
See application file for complete search history.

(56) References Cited

U.S. PATENT DOCUMENTS 7,022,324 B2  4/2006  Binley et al.
7,537,769 B2 * 5/2009  Hone .................. C07K 14/005
                                                      424/196.11

OTHER PUBLICATIONS

Kuwata et al. Short Communication: Construction of Chimeric Simian and Human Immunodeficiency Viruses that Produce Interleukin 12, AIDS Research and Human Retroviruses, Jul. 2004. 16(5): 465-470.*
Xiang et al. Mutagenic Stabilization and/or Disruption of a CD4-Bound State Reveals Distinct Conformations of the Human Immunodeficiency Virus Type 1 gp120 Envelope Glycoprotein. Journal of Virology, 2002. 76 (19):9888-9899.
Dudley et al. A Novel Yeast-based Recombination Method to Clone and Propagate Diverse HIV-1 Isolates. BioTechniques, 2009. 46:458-467.
Genbank Accesssion No. AAB50262.1. Oct. 2002. 5 pages.
Genbank Accesssion No. AB016337. Jul. 2016. 2 pages.

* cited by examiner

Primary Examiner — James D Schultz
Assistant Examiner — Kimberly A Aron
(74) Attorney, Agent, or Firm — Tarolli, Sundheim, Covell & Tummino LLP

(57) ABSTRACT

A method for inducing an immune response against HIV in a subject includes the step of preparing an HIV-1 gp120 envelope protein coding sequence particle having an N425K mutation, introducing the HIV-1 gp120 protein coding sequence particle having an N425K mutation into an expression construct using yeast homologous recombination, transfecting a cell with the expression construct, wherein the HIV-1 particle is secreted by the cell, and administering the secreted HIV-1 particle and a pharmaceutically acceptable carrier to the subject, wherein the secreted HIV-1 particle stimulates an immune response in the subject.

9 Claims, 19 Drawing Sheets

Specification includes a Sequence Listing.

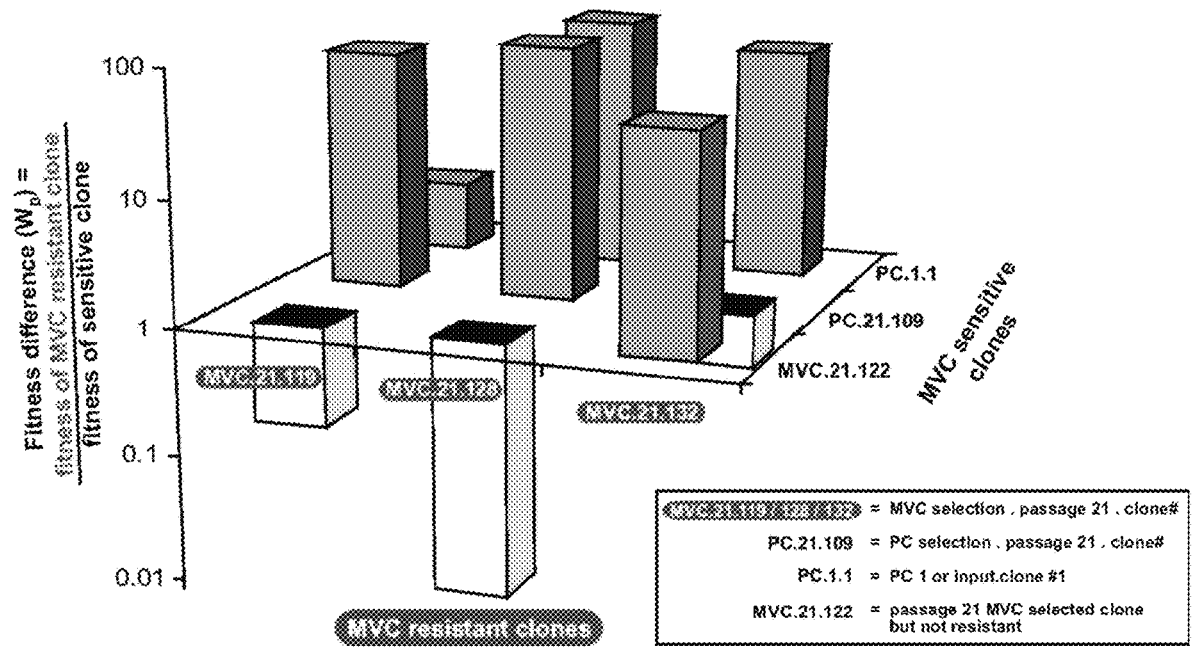
Fig. 7
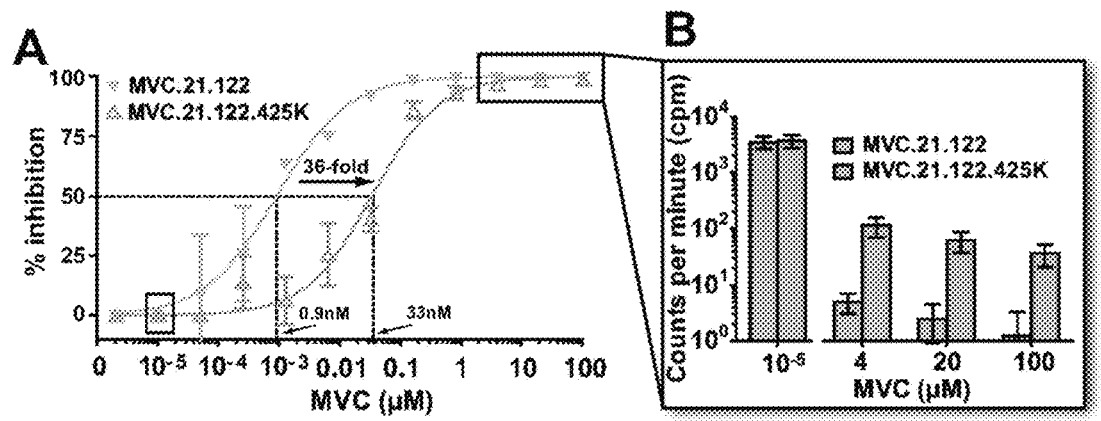
Figs. 8A-B

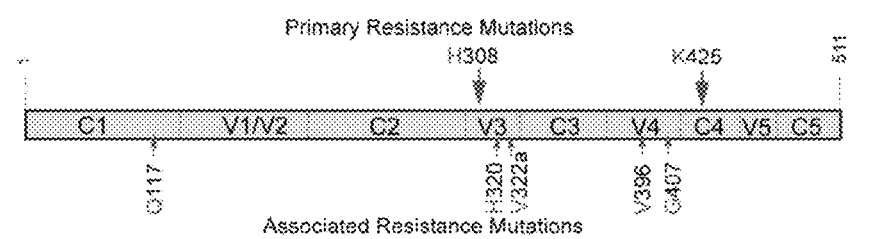
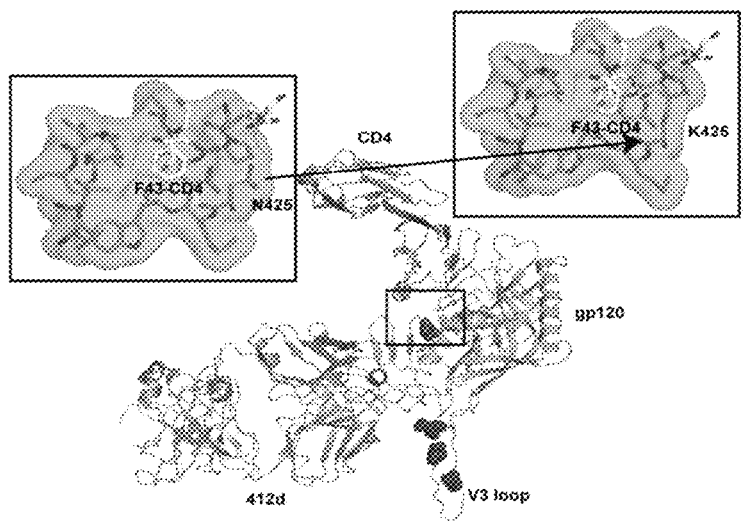
Figs. 10A-B

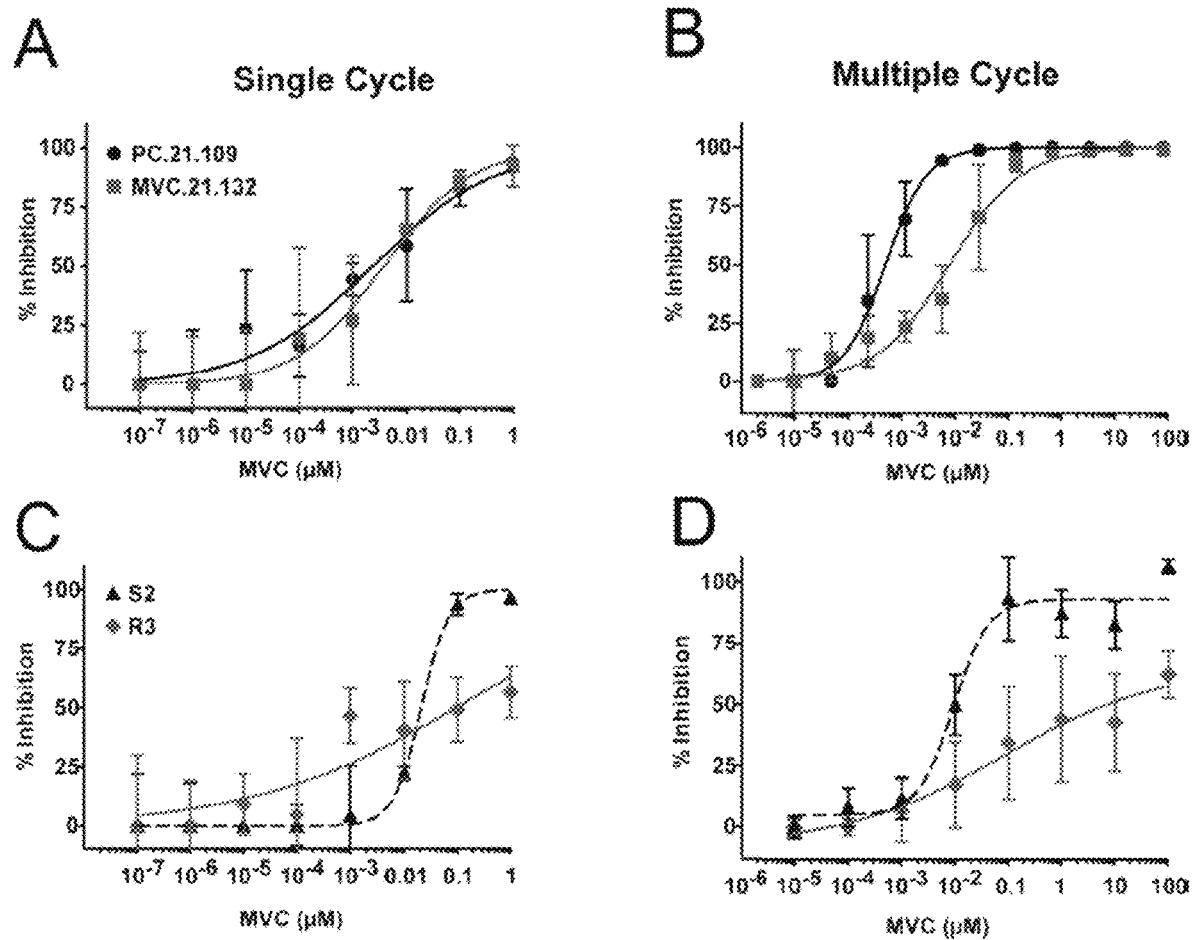
Figs. 11A-D

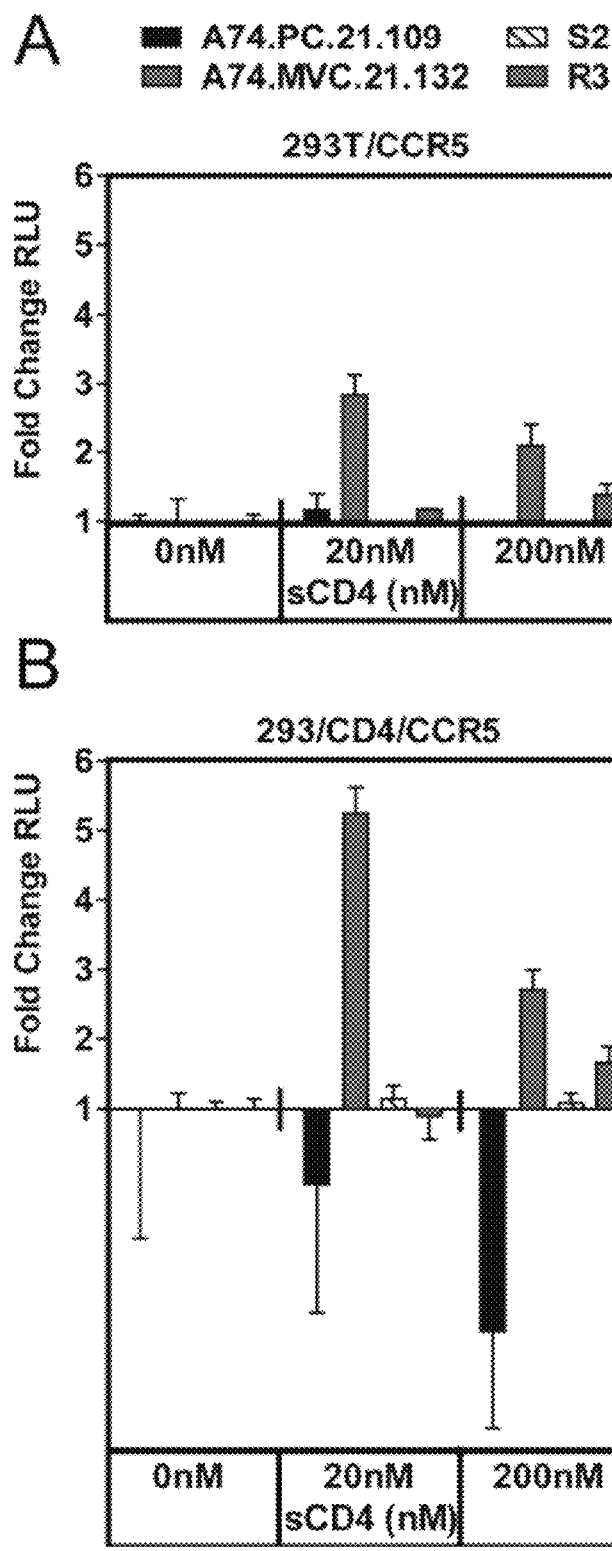
Figs. 12A-B

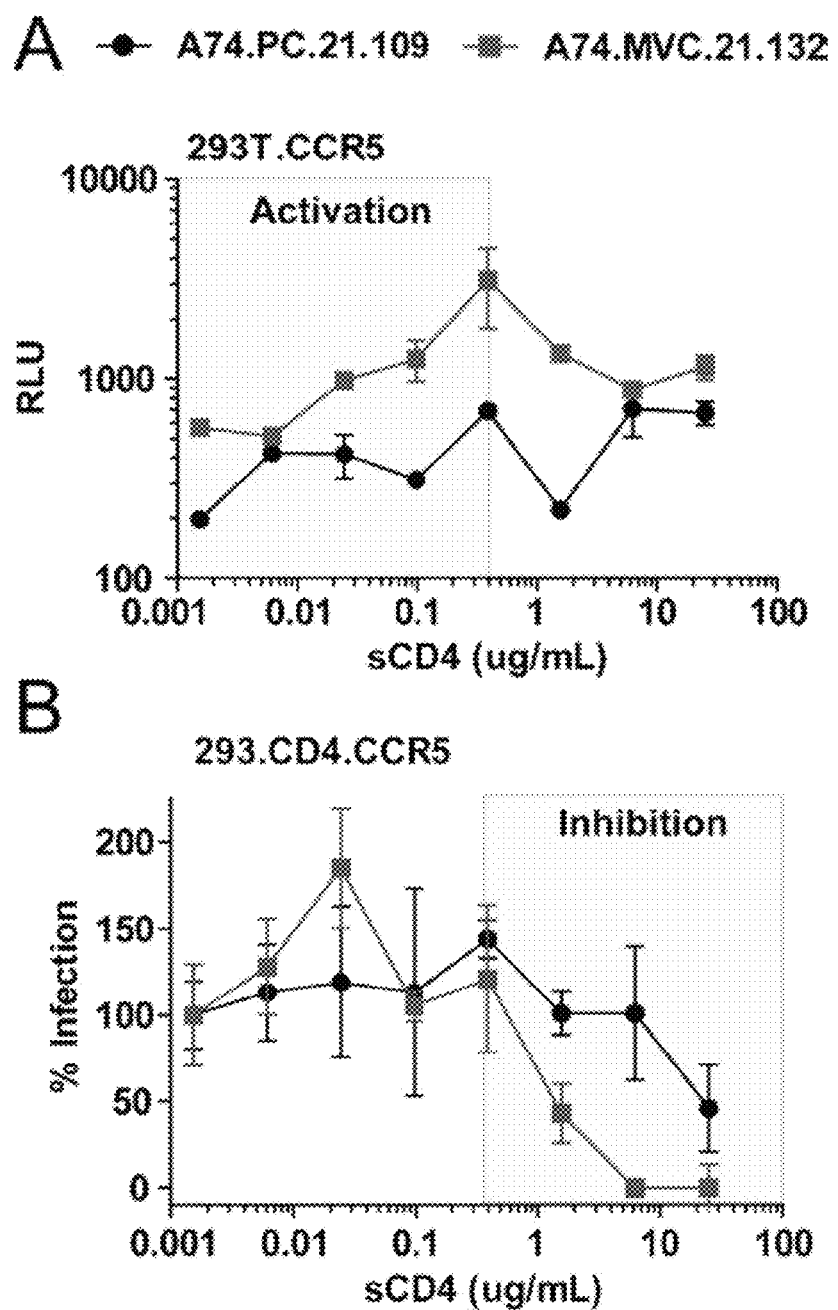
Figs. 13A-B

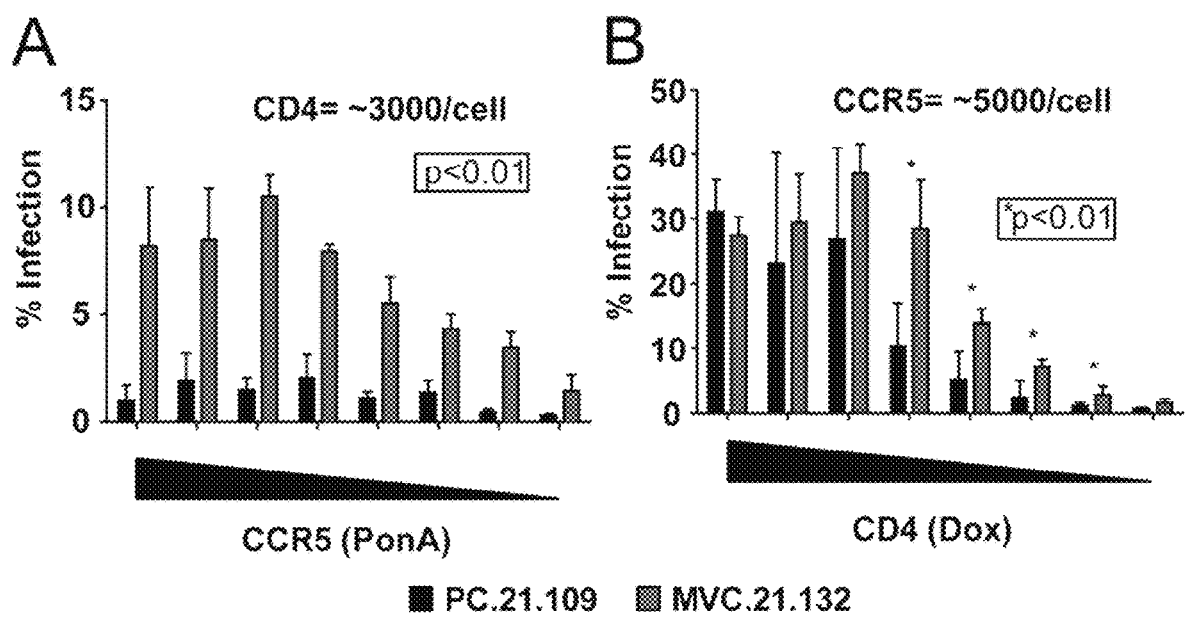
Figs. 14A-B
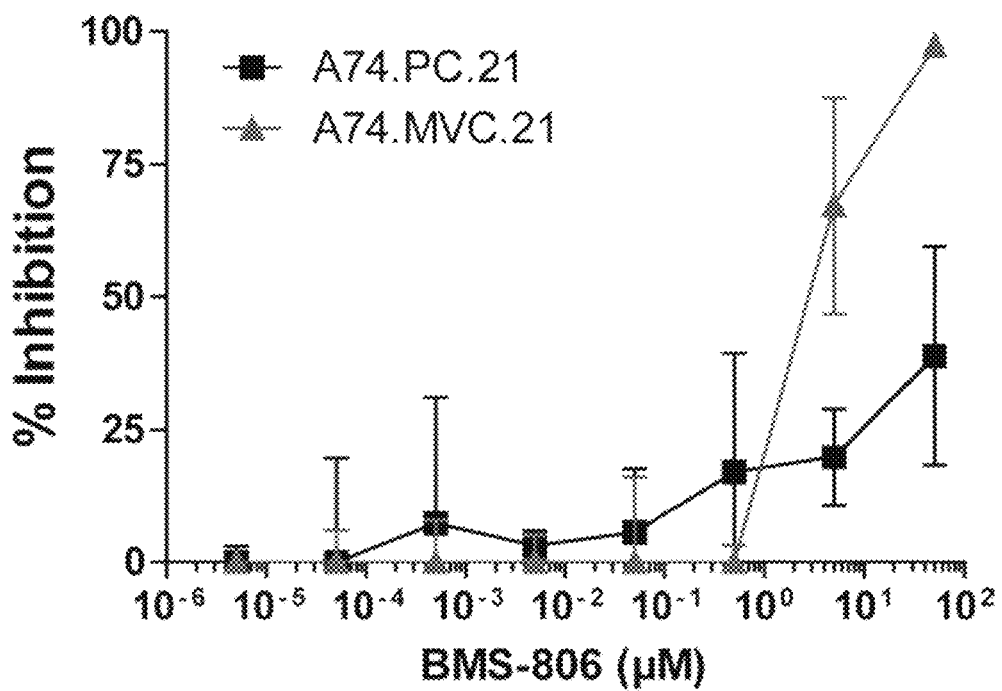
Fig. 15

Fig. 22

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: HIV-1

<400> SEQUENCE: 1
gacaggttaa ttgatagact a                                                  21

<210> SEQ ID NO 2
```

-continued

```
<211> LENGTH: 21
<212> TYPE: DNA
<213> ORGANISM: Artificial Sequence
<220> FEATURE:
<223> OTHER INFORMATION: HIV-1

<400> SEQUENCE: 2
cttcctgctg ctcccaagaa c                                        21

<210> SEQ ID NO 3
<211> LENGTH: 23
<212> TYPE: DNA
<213> ORGANISM: Artificial Sequence
<220> FEATURE:
<223> OTHER INFORMATION: HIV-1

<400> SEQUENCE: 3
ctttttgacc acttgccacc cat                                      23

<210> SEQ ID NO 4
<211> LENGTH: 47
<212> TYPE: DNA
<213> ORGANISM: Artificial Sequence
<220> FEATURE:
<223> OTHER INFORMATION: HIV-1

<400> SEQUENCE: 4
ctactctttg ccacatcttt ataatttgct ttattctgca tggaaga            47

<210> SEQ ID NO 5
<211> LENGTH: 47
<212> TYPE: DNA
<213> ORGANISM: Artificial Sequence
<220> FEATURE:
<223> OTHER INFORMATION: HIV-1

<400> SEQUENCE: 5
tcttccatgc agaataaagc aaattataaa gatgtggcaa agagtag            47
```

HIV-1 VACCINE

RELATED APPLICATION

This application claims priority from U.S. Provisional Application No. 61/895,661, filed Oct. 25, 2013, the subject matter of which is incorporated herein by reference in its entirety.

BACKGROUND

The Human Immunodeficiency Virus (HIV) is the causative agent of Acquired Immunodeficiency Syndrome (AIDS). HIV rapidly undergoes genetic changes to escape from the subject's immune system response. Identification of potent, broadly cross-reactive human monoclonal antibodies to HIV has major implications for development of HIV inhibitors, vaccines, and tools for understanding mechanisms of HIV entry.

Eliciting and boosting immune responses by therapeutic vaccination has been used in HIV-1 patients. However, studies are limited, sample sizes are relatively small, and design of therapeutic vaccines is yet to be improved.

SUMMARY

Embodiments described herein relate to a method for inducing an immune response against HIV in a subject. The method includes the step of preparing an HIV-1 gp120 envelope protein coding sequence particle having an N425K mutation. The method also includes the step of introducing the HIV-1 gp120 protein coding sequence particle having an N425K mutation into an expression construct using yeast homologous recombination. The method also includes the step of transfecting a cell with the expression construct, wherein the HIV-1 particle is secreted by the cell. The method also includes the step of administering the secreted HIV-1 particle and a pharmaceutically acceptable carrier to the subject. The secreted HIV-1 particle stimulates an immune response in the subject.

Other embodiments described herein relate to a vaccine for HIV-1. The vaccine includes a vector. The vector includes a replication defective polynucleotide encoding a gp120 HIV-1 envelope protein having an N425K mutation. The vaccine also includes a pharmaceutically acceptable carrier.

Additional embodiments described herein relate to a method of producing broadly neutralizing CD4i HIV-1 antibodies in a host subject. The method comprises administering to the host subject a vaccine for HIV-1. The vaccine includes a vector. The vector includes a replication defective polynucleotide encoding a gp120 HIV-1 envelope protein having an N425K mutation. The vaccine also includes a pharmaceutically acceptable carrier. The method also includes the step of obtaining a biological sample from the host subject. The sample includes broadly neutralizing CD4i antibodies directed to a CD4 coreceptor biding site of HIV-1 generated by the host in response to the vaccine. The method also includes the step of isolating the broadly neutralizing CD4i antibodies from the sample.

BRIEF DESCRIPTION OF THE DRAWINGS

FIG. 7 illustrates a graph showing the replicative fitness of HIV-1 gp120 chimeric virus clones derived from MVC selected and passage control experiments. The infectious titers of three MVC-resistant clones (MVC.21.119, MVC.21.128, and MVC.21.132) and three MVC-sensitive clones (MVC.21.122, PC.21.109, and PC.1.1) were measured using a standard $TCID_{50}$ assay. A pairwise competition was performed competing the MVC resistant against the sensitive gp120 clones in U87.CD4.CCR5 cells using equal MOI of each virus (0.0001 IU/mL). Infected cells were harvested at peak viremia (day 5) and the relative frequency of each virus in the competition was measured using OLA to distinguish and quantify the amount of one virus versus the other. The fitness difference (or ratio of the relative fitness values) were calculated as described and the results presented in the figure. Shaded bars indicate the resistant clone won the competition whereas no shading indicates the resistant clone lost the competition.

FIGS. 8 (A-B) illustrate a plot and graph showing the effect of the N425K mutation on MVC resistance. (A) Drug sensitivity assays were performed for clone MVC.21.122 and clone MVC.21.122.425K in which the K425 mutation was introduced by site-directed mutagenesis. U87.CD4.CCR5 cells were infected in triplicate with standard deviations shown. Inhibition curves were generated using GraphPad Prism software version 5. (B) Reverse transcriptase activity measured as counts per minute (cpm) for MVC concentrations $1\times10^{-5}$, 4, 20, and 100 µM from which the curves in panel (A) were derived are shown. Data represents triplicates with standard deviations shown. Reverse transcriptase activity was detected at 100 µM MVC for MVC.21.122.425K.

FIGS. 10(A-B) illustrate schema showing maraviroc resistance mutations of R3 and A74.MVC.21 viruses. (A) The maraviroc resistant viruses R3 and A74.MVC.21 differ in their resistance mutations. Virus R3 has a primary resistance mutation H308 in the V3 loop with mutations H320, V322a, and G407 associated with the phenotype. In contrast, A74.MVC.21 contains the primary resistance mutation K425 in the C4 region of gp120 with mutations Q117 and V396 associated. (B) Modeling of K425 into the HIV-1$_{YU-2}$ gp120 structure identified new interactions between K425 and F43 of CD4. Alignment of the YU-2 strain and A74.MVC.21 C4 region of gp120 is shown. Amino acid differences between strains are shown in bold. Resistance mutations for R3 and A74.MVC.21 are indicated as spheres in the structure.

FIGS. 11 (A-D) illustrate plots showing maraviroc resistance profiles in single and multiple cycle assays. Sensitivity of maraviroc resistant viruses A74.MVC.21.132 and R3 were performed in single- and multiple-replication cycle assays. Single replication cycle drug susceptibility assays (panels A and C) were performed in U87.CD4.CCR5 cells using psuedoviruses. Luciferase activity was measured 48 hours after infection and percent inhibition calculated based on the no drug condition. Multiple replication cycle drug susceptibility assays (panels B and D) were performed in U87.CD4.CCR5 cells. Reverse transcriptase activity was quantified and percent inhibition calculated based on the no drug condition. Standard deviations are shown. Curves were generated using curve fitting features of GraphPad Prism 5 software.

FIGS. 12 (A-B) illustrate graphs showing pre-exposure to sCD4 Enhances Infection by A74.MVC.21.132. (A) Psueoviruses were pre-incubated with sCD4 (0, 20, or 200 nM) and then used to infect 293T cells transfected to express CCR5 but lacking cellular CD4. Luciferase activity was measured and compared with the no sCD4 condition. Data represents mean of triplicates with standard deviations. (B) Psuedoviruses were treated as described and used to infect 293.CD4 cells transfected to express CCR5. Luciferase activity was measured and compared with the no sCD4 condition. Data represents mean of triplicates with standard deviations.

FIGS. 13(A-B) illustrate a plot showing enhancement of viral infection and inhibition by sCD4 is concentration dependent. (A) Psuedoviruses were pre-incubated with sCD4 in 4-fold dilutions starting at 25 µg/mL and used to infect 293T cells transfected to express CCR5. Luciferase activity (RLU) was measured 48 hours post infection. (B) Psuedoviruses were pre-incubated with sCD4 in 4-fold dilutions starting at 25 µg/mL and used to infect 293. CD4 cells transfected to express CCR5. Luciferase activity was measured 48 hours post infection. Percent infection was calculated based on the luciferase activity measured for the no sCD4 condition. Data represents means of triplicates with standard deviations shown.

FIGS. 14(A-B) illustrate graphs showing A74.MVC.21.132 Infects Cells Expressing Low Surface Density CD4. (A) 293 Affinofile cells were induced to express low levels of CD4 across a range of CCR5 surface expression levels. Cells were infected with psuedovirus and luciferase activity measured 48 hours post infection. Percent infection was calculated based on the luciferase activity measured for the highest induction of both receptors (not shown). (B) 293 Affinofile cells were induced to express low levels of CCR5 across a range of CD4 surface expression levels and infected with psuedovirus as described. Data represents means of triplicates with standard deviations. * represents $p<0.01$ (one-tailed T test).

FIG. 15 illustrates a plot showing sensitivity to attachment inhibitor BMS-806. Drug susceptibility assays performed in U87.CD4.CCR5 cells with 10-fold dilutions of BMS-806 were performed with sensitive (A74.PC.21) and maraviroc resistant (A74.MVC.21) viruses. Reverse transcriptase activity was measured five days post infection and percent inhibition calculated based on the no drug condition. Data represents means of triplicates with standard deviations.

Figure 22:
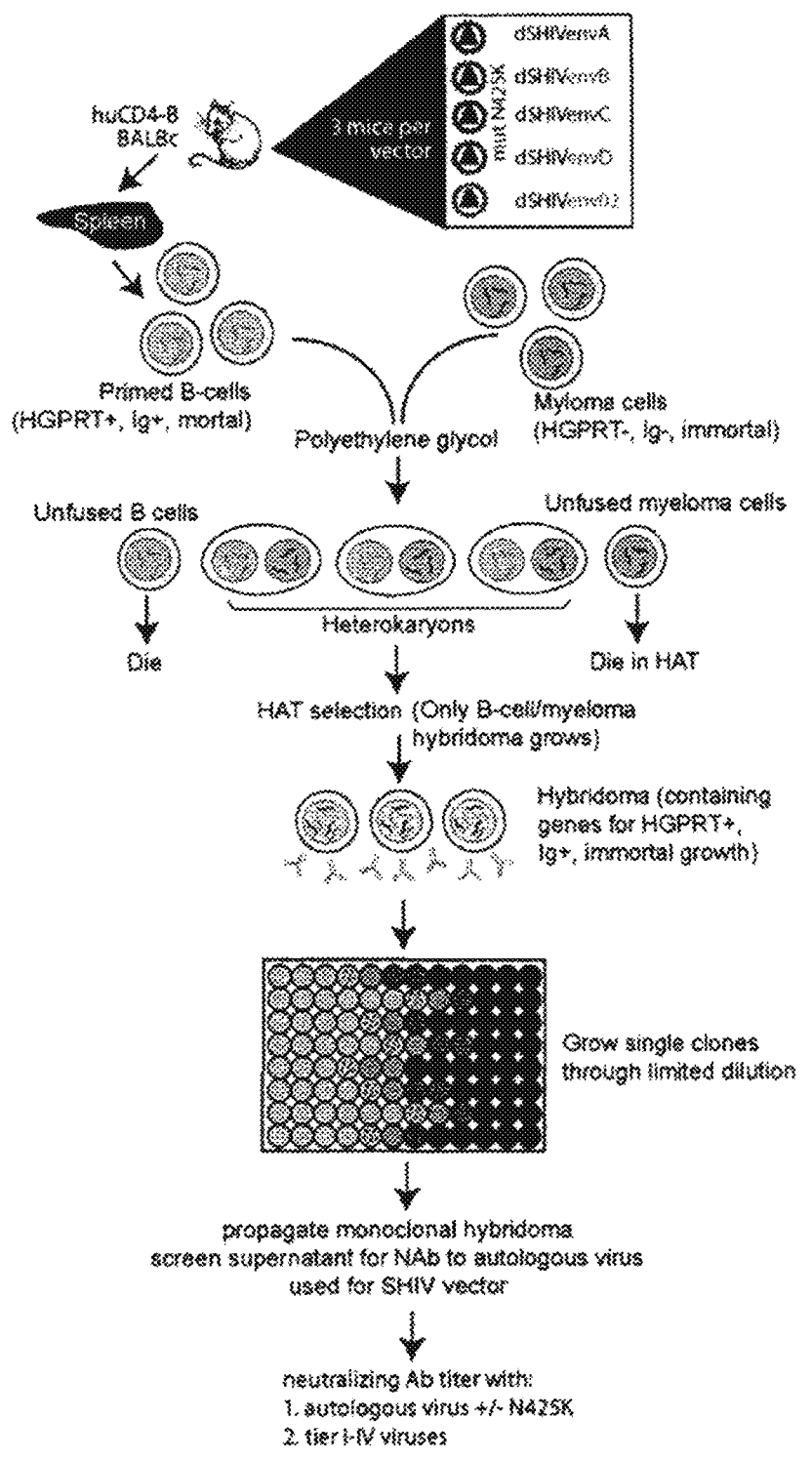

FIG. 22 is a schematic drawing showing the selection of B cell hybridomas in accordance with an aspect of the invention.

DETAILED DESCRIPTION

Figure 1:
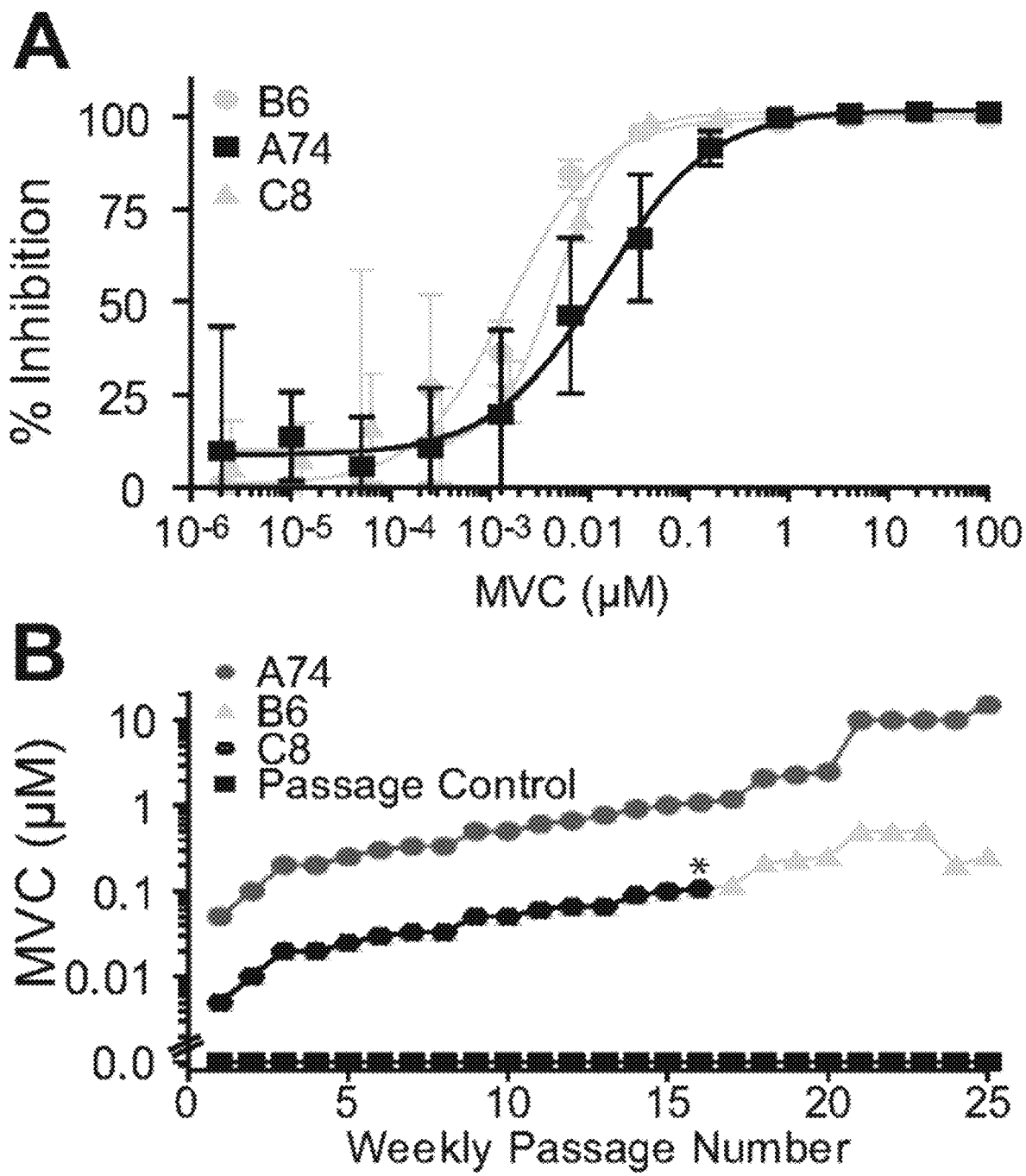
FIGS. 1(A-B) illustrate plots showing maraviroc sensitivity of primary HIV-1 isolates. Viruses representing HIV-1 Subtypes A, B, and C (A) were used to infect U87.CD4.CCR5 in the presence of increasing concentrations of MVC. The data shown are means of triplicates with error bars representing standard deviations. (B) Viruses A74, B6 and C8 were passaged in U87.CD4.CCR5 cells weekly in the presence of increasing concentrations of MVC to select for a MVC escape mutant. Cultures were monitored for reverse transcriptase activity as described in Materials and Methods. Cultures for virus C8 were abandoned at week 16 (*) when no RT activity was measured.

It should be understood that the present invention is not limited to particular methods, reagents, compounds, compositions or biological systems, which can, of course, vary. It should also to be understood that the terminology used herein is for the purpose of describing particular aspects of the present invention only, and is not intended to be limiting. Unless defined otherwise, all technical and scientific terms used herein have the same meaning as commonly understood by one of ordinary skill in the art to which the present invention pertains. Although any methods and materials similar or equivalent to those described herein can be used in the practice of the present invention, the preferred materials and methods are described herein. In describing and claiming the present invention, the following terminology will be used.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the present invention.

The term "construct" refers to a recombinant nucleotide sequence, generally a recombinant nucleic acid molecule, that has been generated for the purpose of the expression of a specific nucleotide sequence(s), or is to be used in the construction of other recombinant nucleotide sequences.

The term "gene" refers to a nucleic acid comprising a nucleotide sequence that encodes a polypeptide or a biologically active ribonucleic acid (RNA) such as a tRNA, shRNA, miRNA, etc. The nucleic acid can include regulatory elements (e.g., expression control sequences such as promoters, enhancers, an internal ribosome entry site (IRES)) and/or introns. A "gene product" or "expression product" of a gene is an RNA transcribed from the gene (e.g., pre- or post-processing) or a polypeptide encoded by an RNA transcribed from the gene (e.g., pre- or post-modification).

The terms "gene of interest," "nucleotide sequence of interest" and "nucleic acid of interest" refer to any nucleotide or nucleic acid sequence that encodes a protein or other molecule that is desirable for expression in a host cell (e.g., for production of the protein or other biological molecule (e.g., an RNA product) in the target cell). The nucleotide sequence of interest is generally operatively linked to other sequences which are needed for its expression, e.g., a promoter. Further, the sequence itself may be regulatory in nature and thus of interest for expression of biologies in the target cell.

The term "infectious" in reference to a recombinant lentivirus or lentiviral particle, indicates that the lentivirus or lentiviral particle is able to enter cells and to perform at least one of the functions associated with infection by a wild-type lentivirus, e.g., release of the viral genome in the host cell cytoplasm, entry of the viral genome into the nucleus, reverse transcription, and/or integration of the viral genome into the host cell's DNA. It is not intended to indicate that the virus or viral particle is capable of undergoing replication or of completing the viral life cycle. Similarly, the term "infectivity" as used herein in reference to a recombinant lentiviral vector construct, lentivirus or lentiviral particle indicates the ability or the enhanced ability to enter cells and to perform at least one of the functions associated with infection by a wild-type lentivirus. For example, the term "enhanced infectivity" or "enhancing the infectivity" as used herein in reference to a recombinant lentiviral vector construct, lentivirus or lentiviral particle indicates the enhanced or significantly measurable increase in the ability to enter cells and to perform at least one of the functions associated with infection by a wild-type lentivirus compared to a control recombinant lentiviral vector construct, lentivirus or lentiviral particle (e.g., a recombinant lentiviral vector construct, lentivirus or lentiviral particle not comprising a GRPE element).

The term "nucleic acid" refers to polynucleotides such as DNA or RNA. Nucleic acids can be single-stranded, partly or completely, double-stranded, and in some cases partly or completely triple-stranded. Nucleic acids include genomic DNA, cDNA, mRNA, etc. Nucleic acids can be purified from natural sources, produced using recombinant expression systems and optionally purified, chemically synthesized, e.g., iRNA, siRNAs, microRNAs, and ribonucleoproteins. Where appropriate, e.g., in the case of chemically synthesized molecules, nucleic acids can comprise nucleoside analogs such as analogs having chemically modified bases or sugars, backbone modifications, etc. The term "nucleic acid sequence" as used herein can refer to the nucleic acid material itself and is not restricted to the sequence information (i.e., the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated. The term "nucleic acid segment" is used herein to refer to a nucleic acid sequence that is a portion of a longer nucleic acid sequence.

The terms "operably linked" and "operably associated" refer to a functional relationship between two nucleic acids, wherein the expression, activity, localization, etc., of one of the sequences is controlled by, directed by, regulated by, modulated by, etc., the other nucleic acid. The two nucleic acids are said to be operably linked or operably associated or in operable association. "Operably linked" or "operably associated" can also refer to a relationship between two polypeptides wherein the expression of one of the polypeptides is controlled by, directed by, regulated by, modulated by, etc., the other polypeptide. Typically a first nucleic acid sequence that is operably linked to a second nucleic acid sequence, or a first polypeptide that is operatively linked to a second polypeptide, is covalently linked, either directly or indirectly, to such a sequence, although any effective three-dimensional association is acceptable. One of ordinary skill in the art will appreciate that multiple nucleic acids, or multiple polypeptides, may be operably linked or associated with one another.

The term "plasmid" refers to a circular nucleic acid vector. Plasmids contain an origin of replication that allows many copies of the plasmid to be produced in a bacterial or eukaryotic cell (e.g., 293T producer cell) without integration of the plasmid into the host cell DNA.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

The term "packaging" refers to the process of sequestering (or packaging) a viral genome inside a protein capsid, whereby a virion particle is formed. This process is also known as encapsidation. As used herein, the term "packaging signal" or "packaging sequence" refers to sequences located within the retroviral genome which are required for insertion of the viral RNA into the viral capsid or particle. Several retroviral vectors use the minimal packaging signal (also referred to as the psi "Ψ" sequence) needed for encapsidation of the viral genome. Thus, as used herein, the terms "packaging sequence," "packaging signal," "psi" and the symbol "Ψ" are used in reference to the non-coding sequence required for encapsidation of retroviral RNA strands during viral particle formation. The term includes naturally occurring packaging sequences and also engineered variants thereof. Primary packaging signals of a number of different retroviruses, including lentiviruses, are known in the art.

The term "recombinant" refers to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus or viral particle is one that comprises a recombinant nucleic acid. A recombinant cell is one that comprises a recombinant nucleic acid.

The terms "regulatory sequence" and "regulatory element" refer to a nucleic acid sequence that regulates one or more steps in the expression (particularly transcription, but in some cases other events such as splicing or other processing) of nucleic acid sequence(s) with which it is operatively linked. The terms include promoters, enhancers and other transcriptional control elements that direct or enhance transcription of an operatively linked nucleic acid. Regulatory sequences may direct constitutive expression (e.g., expression in most or all cell types under typical physiological conditions in culture or in an organism), cell type specific, lineage specific, or tissue specific expression, and/ or regulatable (inducible or repressible) expression.

The term "retrovirus" refers to any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). "Retroviruses" of the invention also include human T cell leukemia viruses, HTLV-1 and HTLV-2, and the lentiviral family of retroviruses, such as Human Immunodeficiency Viruses, HIV-1, HIV-2, simian immnodeficiency virus (SIV), feline immnonodeficiency virus (FIV), equine immnodeficiency virus (EIV), and other classes of retroviruses.

Retroviruses are RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions, appears at both the both the 5' and 3' ends of the viral genome. In one embodiment of the invention, the promoter within the LTR, including the 5' LTR, is replaced with a heterologous promoter. Examples of heterologous promoters which can be used include, for example, the cytomegalovirus (CMV) promoter.

The term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

The term "hybrid" refers to a vector, LTR or other nucleic acid containing both lentiviral sequences and non-lentiviral retroviral sequences.

The term "transfection" refers to the introduction of foreign DNA into eukaryotic cells. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "transduction" refers to the delivery of a gene(s) using a viral or retroviral vector by means of viral infection rather than by transfection. In preferred embodiments, retroviral vectors are transduced by packaging the vectors into virions prior to contact with a cell.

The term "promoter/enhancer" refers to a segment of DNA which contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The term "retroviral vector" refers to a vector containing structural and functional genetic elements that are primarily derived from a retrovirus.

The term "lentiviral vector" refers to a vector containing structural and functional genetic elements outside the LTRs that are primarily derived from a lentivirus.

A retroviral vector is considered a "lentiviral vector" if at least approximately 50% of the retrovirus derived long terminal repeat, LTR (e.g., 5'LTR and/or 3' LTR) and primary packaging sequences (e.g., $\Psi$) in the vector are derived from a lentivirus and/or if the LTR and primary packaging sequences are sufficient to allow an appropriately sized nucleic acid comprising the sequences to be reverse transcribed and packaged in a mammalian or avian cell that expresses the appropriate lentiviral proteins. Typically, LTR and primary packaging sequences derived from a lentivirus for use in a lentiviral vector of the invention may be at least approximately 50%, approximately 60%, approximately 70%, approximately 80%, approximately 90%, or identical to lentiviral LTR and primary packaging sequences. In certain embodiments of the invention between approximately 90 and approximately 100% of the LTR and primary packaging sequences are derived from a lentivirus. For example, the LTR and primary packaging sequences may be between approximately 90% and approximately 100% identical to lentiviral LTR and primary packaging sequences.

The term "RNAi agent" refers to an at least partly double-stranded RNA having a structure characteristic of molecules that are known in the art to mediate inhibition of gene expression through an RNAi mechanism or an RNA strand comprising at least partially complementary portions that hybridize to one another to form such a structure. When an RNA comprises complementary regions that hybridize with each other, the RNA will be said to self-hybridize. An RNAi agent includes a portion that is substantially complementary to a target nucleic acid sequence or gene. An RNAi agent optionally includes one or more nucleotide analogs or modifications. One of ordinary skill in the art will recognize that RNAi agents that are synthesized in vitro can include ribonucleotides, deoxyribonucleotides, nucleotide analogs, modified nucleotides or backbones, etc., whereas RNAi agents synthesized intracellularly, e.g., encoded by DNA templates, typically consist of RNA, which may be modified following transcription. Of particular interest herein are short RNAi agents, i.e., RNAi agents consisting of one or more strands that hybridize or self-hybridize to form a structure that comprises a duplex portion between about 15-29 nucleotides in length, optionally having one or more mismatched or unpaired nucleotides within the duplex. RNAi agents include short interfering RNAs (siRNAs), short hairpin RNAs (shRNAs), and other RNA species that can be processed intracellularly to produce shRNAs including, but not limited to, RNA species identical to a naturally occurring miRNA precursor or a designed precursor of an miRNA-like RNA.

The terms "vector" and "vector construct" refer to a nucleic acid molecule capable of transferring or transporting another passenger DNA or RNA nucleic acid molecule (i.e., a sequence or gene of interest) into a host cell. For instance, either a DNA or RNA vector can be used to derive viral particles. Similarly, a cDNA copy can be made of a viral RNA genome. Alternatively, a cDNA (or viral genomic DNA) moiety can be transcribed in vitro to produce RNA. These techniques are well-known to those skilled in the art, and also are described. The transferred nucleic acid (i.e., a sequence or gene of interest) is generally linked to, e.g., inserted into, the vector nucleic acid molecule. A vector may include sequences that direct autonomous replication in a cell, or may include sequences sufficient to allow integration into host cell DNA. The vector is not a wild-type strain of a virus, inasmuch as it comprises human-made mutations or modifications. Thus, the vector typically is derived from a wild-type viral strain by genetic manipulation (e.g., by addition, deletion, mutation, insertion or other techniques known in the art) to comprise lentiviral vectors, as further described herein. In some embodiments of the present invention, the lentiviral vector constructs for use in a pharmaceutical composition (e.g., a vaccine) comprise those lentiviral vectors in which the lentiviral integrase function has been deleted and/or abrogated by site directed mutagenesis. Useful vectors include, for example, plasmids (typically DNA plasmids, but RNA plasmids are also of use), phages, cosmids, and viral vectors.

The term "viral vector" refers to either a nucleic acid molecule (e.g., a plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s). In particular, the terms "lentiviral vector," "lentiviral expression vector," etc. may be used to refer to lentiviral particles and/or lentiviral transfer plasmids of the invention as described herein. The phrase "essential lentiviral protein" as used herein refers to those viral protein(s), other than envelope protein, that are required for the lentiviral life cycle. Essential lentiviral proteins may include those required for reverse transcription and integration and for the packaging (e.g., encapsidation) of a retroviral genome.

The terms "subject," "patient," "individual," and "host" used interchangeably herein, refer to a mammal, including, but not limited to, murines, felines, simians, humans, mammalian farm animals, mammalian sport animals, and mammalian pets. The term includes mammals that are infected with as well as those that are susceptible to infection by an immunodeficiency virus. In certain embodiments, the term refers to a human infected with HIV.

"HIV" is used herein to refer to the human immunodeficiency virus. It is recognized that the HIV virus is an example of a hyper-mutable retrovirus, having diverged into two major subtypes (HIV-1 and HIV-2), each of which has many subtypes. In some embodiments, a human subject is infected with the HIV-1 subtype.

As used herein, the term "viral infection" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses, e.g., HIV-1, is also a possible result of viral infection.

Embodiments described herein relate to HIV-1 based vaccine constructs that include a N425K mutation in the gp120 envelope protein encoding sequence and that when administered to a subject are capable of eliciting an immune response in the subject. In other embodiments, the vaccine constructs can be used to generate and/or screen for broadly neutralizing anti-HIV antibodies.

Using HIV-1 gp120 envelope protein encoding sequences from maraviroc resistant (MVC-resistant) cultures cloned into NL4-3 backbone and SHIV vectors via yeast-based recombination, it was found that HIV-1 viral resistance was dependent upon a single mutation in the C4 region of gp120 (K425) which significantly increases CD4 binding by the virus. Modeling studies showed a stabilized and enhanced CD4 interaction via a new H bond and a cation-π interaction between the side chains of K425 in gp120 and F43 in CD43 in CD4.

Figure 17:
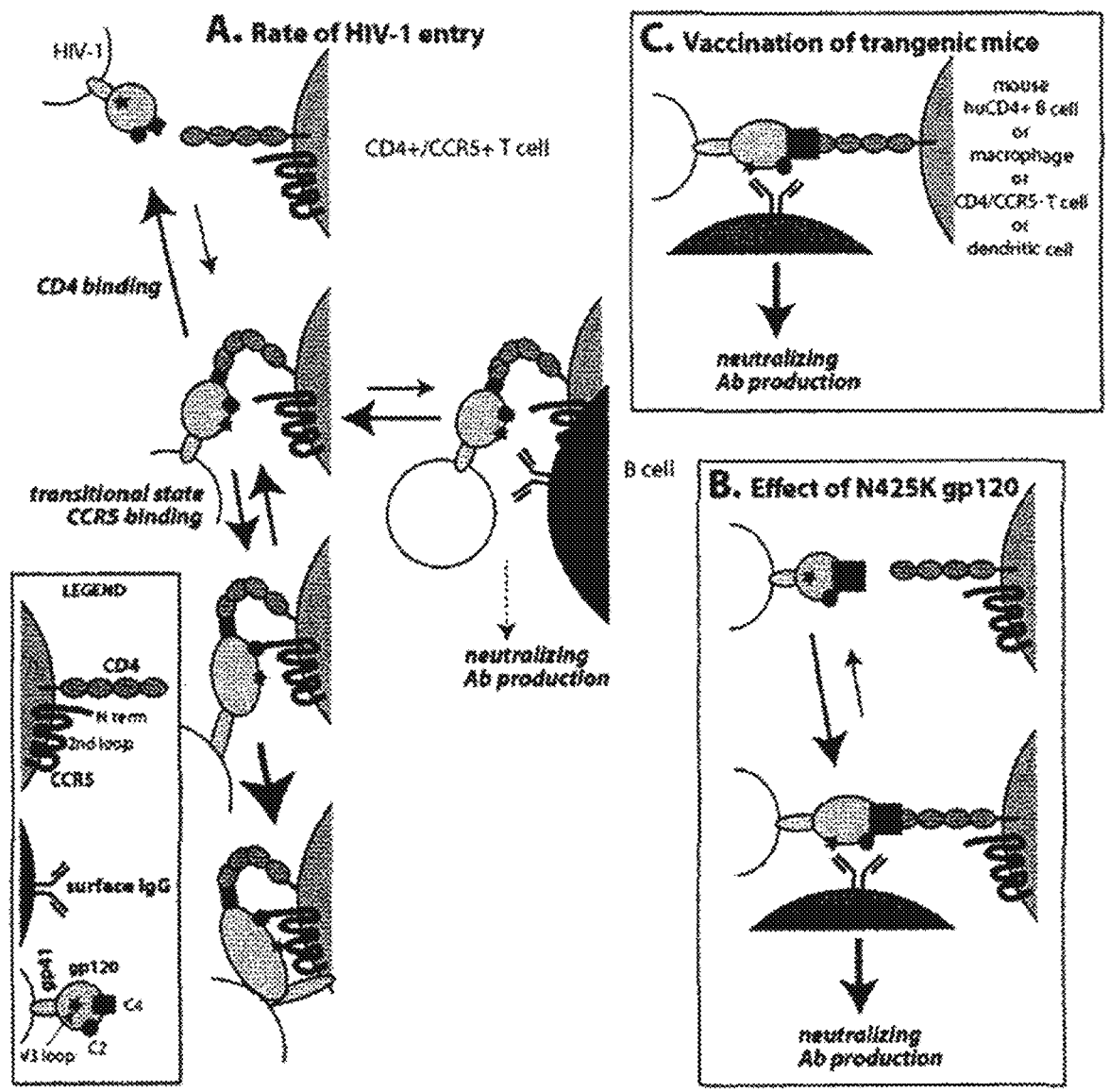
FIG. 17 illustrates a schematic showing recognition of CD4i epitopes by immature B cells.

Without being bound by theory, it is believed that the increased CD4 binding affinity resulting from the N425K mutation can lock gp120 in a transitional state prior to interactions with a coreceptor (e.g., CCR5) (see FIG. 17). It is further believed that the increased CD4 binding affinity leads to enhanced antigen presentation by CD4+ dendritic cells or macrophages and can increase exposure to the more conserved and functional CD4 induced (designated CD4i) epitopes allowing for an effective humoral response including the production of CD4i broadly neutralizing antibodies.

In some embodiments, the HIV-1 based vaccine constructs can include at least one recombinant HIV-1 particle prepared from an HIV-1 RNA sample obtained from an HIV-1 virus having an N425K mutation in the gp120 envelope protein encoding sequence. HIV-1 particles described herein can include viral Gag, Pol, and Env proteins and a viral genome that comprises a nucleic acid including a GRPE element and sequences sufficient for reverse transcription and packaging may be used to deliver transgenic material to a target cell. The viral genome may further comprise regulatory sequences sufficient to promote transcription of an operably linked sequence of interest. The recombinant HIV-1 particles are replication-defective, i.e., the viral genome does not encode functional forms of all the proteins necessary for the infective cycle. For example, sequences encoding a structural protein or a protein required for replication may be mutated or disrupted or may be partly or completely deleted and/or replaced by a different nucleic acid sequence, e.g., a nucleic acid sequence of interest that is to be introduced into a target cell. However, sequences required for reverse transcription, integration, and packaging are typically functional.

Any HIV-1 gag (group-specific antigen) protein coding sequence derived from an HIV-1 virus can be used. Exemplary gag protein coding sequences derived from an HIV-1 virus include gag protein coding sequences for the precursor gag polyprotein which is processed by viral protease during maturation to MA (matrix protein, p17); CA (capsid protein, p24); SP1 (spacer peptide 1, p2); NC (nucleocapsid protein, p7); SP2 (spacer peptide 2, p1) and P6 protein.

Any HIV-1 pol protein coding sequence derived from an HIV-1 virus can be used. Exemplary pol protein coding sequences derived from an HIV-1 virus include pol protein coding sequences for viral enzymes reverse transcriptase (RT) and RNase H, integrase (IN), and HIV protease (PR).

Any HIV-1 envelope protein coding sequence derived from an HIV-1 virus having an N425K mutation that mediates membrane fusion and increases CD4 binding affinity can be used. As used herein, the term "HIV-1 envelope protein" refers to a full-length protein, fragment, analog, or derivative thereof. The HIV-1 RNA can include an HIV-1 protein coding sequence that comprises HIV-1 gp120 envelope (env) protein coding sequence having an N425K mutation.

HIV-1 envelope protein coding sequences useful in the present method can include, but are not limited to HIV-1 envelope protein coding sequences encoding surface proteins having an N425K mutation from a number of different HIV-1 groups. Exemplary HIV-1 groups include both the "major" group (i.e., the M group) and the minor groups O, N and P. An HIV-1 envelope protein having an N425K mutation can also include subgroups, or clades, of HIV-1 groups known in the art.

In some embodiments, the HIV-1 envelope protein having an N425K mutation is an HIV-1 group M, subtype B envelope protein variant. Non-limiting examples of subtype B HIV-1 variants can include HIV-1B-92BR014, HIV-1B-92TH593, HIV-1B-92US727, and HIV-1B-92US076.

In some embodiments, the HIV-1 envelope protein coding sequences encode surface proteins having an N425K mutation from HIV-1 group M non-subtype B variant. Non-B HIV-1 group M variants can include the clades or subtypes A, C, D, F, G, H, J, K, N and circulating recombinant forms derived from recombination between viruses of different subtypes. Non-limiting examples of non-B HIV-1 subtypes include three subtype A (HIV-1A-93RW024, HIV-1A-92UG031, and HIV-1A-92UG029), four subtype C (HIV-1C-96USNG58, HIV-1C-93MW959, HIV-1C-98IN022, and HIV-1C-92BR025), five subtype D (HIV-1D-92UG021, HIV-1D-92UG024, HIV-1D-94UG114, HIV-1D-92UG038, and HIV-1D-93UG065), two subtype F (HIV-1F-93BR20 and HIV-1F-93BR29), two subtype G (HIV-1G-RU132 and HIV-1G-RU570), and six circulating recombinant forms (HIV-1AE-CMU02, HIV-1AE-CMU06, HIV-1AE-92TH021, HIV-1AE-93TH051, HIV-1AE-95TH001, and HIV-1BF-93BR029). In certain embodiments, the HIV-1 envelope protein coding sequences encode surface proteins from subtype A, B, C, D and CRF02_AG. In some particular embodiments, the HIV-1 envelope protein having an N425K mutation is an HIV-1 group M, subtype A envelope protein variant.

HIV-1 RNA encoding a gp120 surface protein having an N425K mutation can be obtained from HIV-1 virus where resistance was selected to MVC using a dose escalation during a 21 week passage of CCR5-using HIV-1 isolates as described in the Examples below. In some embodiments, selected viral HIV-1 RNA encoding a gp120 surface protein having an N425K mutation can be purified from pelleted virus particles using well known methods. In one example, plasma viral HIV-1 RNA can be purified from pelleted virus particles by centrifuging one milliliter of a patient's plasma at 20,000 g×60 min at 4° C. using a QIAamp Viral RNA Mini Kit (Qiagen).

Once the HIV-1 RNA is obtained and purified it can be reverse transcribed into HIV-1 cDNA. A representative protocol for the preparation of HIV-1 cDNA from purified HIV-1 RNA includes adding 10 µl of the backward (BWD) primer EXT TAT REC CON BWD 13 having SEQ ID NO: 47 to 7.25 µl of DEPC-treated H$_2$O, 2.0 µl of RT Buffer 10× and 2.0 µl of 10 mM dNTP mix. This mixture is further added to 5 µl of purified HIV-1 RNA and 4 µl of PCR water and incubated at 88° C. for 1 minute, 65° C. for 10 minutes, and then 25° C. for 5 min. The resulting mixture is then kept at room temperature. Next, 2.0 µl of 100 mM DTT, 0.25 µl (10U) RNase inhibitor, and 0.5 µl AccuScript High-Fidelity Reverse Transcriptase (AccuRT) (STRATAGENE) is added individually to the mixture. The mixture is then incubated at 42° C. for 90 min, heat inactivated at 70° for 15 minutes, and chilled and held at 4° for PCR amplification. Alternatively, the mixture can be frozen at −20° for later amplification.

A portion of the HIV-1 cDNA corresponding to an HIV-1 env protein coding sequence having a N425K mutation can be amplified using a PCR assay where the HIV-1 cDNA acts as a template. In some embodiments, PCR amplification of the envelope protein coding sequence having a N425K mutation amplifies a portion of the env gene from gp120 up to Tat exon 2. In some embodiments, PCR amplification of the envelope protein coding sequence amplifies a 2302 nt fragment of the HIV-1 env gene, including the entire surface glycoprotein (gp120) having a N425K mutation and most of the transmembrane glycoprotein (gp41) such that recombinant particles produced by forced recombination only contain breakpoints in the gp41 region.

The use of both external and nested env gene specific primers (i.e., a nested PCR) can be employed to amplify an HIV-1 envelope protein coding sequence of HIV-1 cDNA encoding gp120 having a N425K mutation. Amplified PCR products corresponding to a selected HIV-1 gp120 N425K mutant envelope protein coding sequence can then be purified. For example, PCR cDNA products corresponding to the gp120/gp41-coding regions of an HIV-1 gp120 N425K mutant envelope protein can be purified using a QIAquick PCR Purification Kit (QIAGEN).

The resulting HIV-1 gp120 N425K mutant envelope protein coding sequence can be introduced into an expression construct using a yeast based homologous recombination/gap repair method.

An expression construct can include a vector, such as a plasmid. A suitable vector includes at least one origin of replication, a region of the DNA that is substantially identical to the primer binding site (pbs) of HIV-1, a selectable gene replacing at least a portion of the env gene of HIV-1, and a region of DNA that is substantially identical to the 3' end of the long terminal repeat region of HIV. By "substantially identical", it is meant that the regions have sufficient homology with the named segments of DNA as to be able to hybridize under stringent conditions.

A suitable vector can also comprise a partial retrovirus genome, specifically; a vector can include a near full length (nfl) HIV-1 genome devoid of the 5' LTR. Lack of a 5' LTR allows the HIV-1 genome to be located precisely in front of the CMV promoter in the vector such that transcription would be initiated at the first nucleotide of the primer binding site. Cloning the HIV-1 sequence in this way could not be performed with restriction enzymes but can be performed by yeast recombination. In addition a vector devoid of the HIV-1 5' LTR is unable to produce infectious virus. Vectors can include the essential elements for plasmid growth in bacteria and for HIV-1 expression in human cells.

In addition, the yeast-based cloning system allows for cloning into SIVmac, SIVcpz, and SHIV molecular clones. SHIV is an engineered chimeric virus with the envelope of human immunodeficiency virus and the cytoplasm and nucleus of simian immunodeficiency virus (SIV) and is used in animal models to better mimic HIV compared SIV. Therefore, in certain embodiments, SHIV molecular clones are employed.

Vectors can include a sequence corresponding to a near full length HIV-1 backbone. In some embodiments, the near full length HIV-1 backbone includes a HIV-1 Group M subtype A backbone (e.g., HIV-1$_{NL4-3}$). In certain embodiments, the vector can recombine with not only homologous env, gag and/or pol protein coding sequences derived from Maravoc resistant strains of HIV-1 but also from sequences derived from patients infected with other non-A HIV-1 group M subtypes.

In certain embodiments, the near full length HIV-1 yeast-based vector pREC nfl HIV-1 Δenv/URA3 is employed. pREC nfl HIV-1 Δenv/URA3 contains the selection marker URA3. URA3 encodes the orotidine-5'-phosphate decarboxylase protein involved in the biosynthesis of uracil. To prepare pREC nfl HIV-1 Δenv/URA3, URA3 is recombined in yeast to replace a section of the env gene in the pREC nfl HIV-1 vector resulting in a vector having the pREC nfl HIV-1 sequence except with a URA3 gene inserted into and replacing a portion of the envelope gene. Successful recombinants may be selected by growing the yeast transformed with the URA3 and the pREC nfl HIV-1 on uracil-deficient media. In certain embodiments, at least a portion of the 5' and 3' ends of the pREC nfl HIV-1 env gene remain so as to permit further recombination.

In addition to URA3, a pREC nfl HIV-1 Δenv/URA3 vector can also include a yeast transformation selection marker gene that does not replace a portion of the envelope gene (e.g., LEU2 or TRP1).

Expression constructs can be made, for example, by replacing various portions of the HIV-1 env, gag and/or pol gene in the pREC nfl HIV-1 vector with a selectable marker such as URA3. URA3 may be inserted into the pREC nfl HIV-1 vector at different sites for replacement of the gp120/gp41, the gp120, or V3 coding sequence in the HIV-1 envelope gene, for example. In some embodiments, expression constructs are provided that only include break points in the gp41 region. In some embodiments, the HIV-1 env PCR product encoding a gp120 protein having aN425K mutation will be co-transfected into yeast with a linearized pREC nfl$_{NL4-3}$ Δgp120MSD-gp41ecto/URA3+LEU2 vector or a linearized pREC Δgag-pol-SHIVenvΔgp120MSD-gp41ecto/URA3+LEU2 SHIV homolog vector.

To insert a purified HIV-1 gp120 N425K mutant envelope protein coding sequence and replace a selectable gene encoded by the vector, a yeast strain (e.g., Strain BY4727) may be transformed with either linearized or non-linearized pREC_nfl_HIV-1Δproteome/URA3 or SHIV homolog, using a lithium acetate technique for example, along with the purified HIV-1 protein coding cDNA sequence including a N425K mutation. The N425K mutant gp120 envelope protein cDNA recombines with the remaining portions of the env gene flanking the URA3 gene in pREC nfl HIV-1 Δproteome/URA3. The resulting recombinants contain a near full length HIV-1 sequence from the NL4-3 HIV-1 strain, with a N425K mutant gp120 envelope protein encoding gene fragment replacing the env gene of NL4-3.

In some embodiments, PCR products spanning the gp120 N425K mutant/gp41-coding region of HIV-1 are introduced via yeast homologous recombination into a pRECnfl ΔEnv/URA3 vector. The pRECnfl-TRPΔEnv/URA3 vector includes a near-full length HIV-1 genome where a yeast uracil biosynthesis (URA3) gene has replaced the native gp120/gp41 HIV-1 coding sequence. Following successful yeast homologous recombination of the gp120/gp41-coding region of HIV-1 including a N425K mutation and the pRECnfl-TRPΔEnv/URA3 vector, the vector construction expresses all HIV-1 coding regions, that is, all genes corresponding to the HIV-1$_{NFL4-3}$ strain used as backbone in the vector plus the HIV-1 envelope protein coding sequence including a N425K mutation; however, it is unable to produce infectious virus since it is missing the 5' LTR region. In another embodiment, PCR products spanning the gp120/gp41-coding region of HIV-1 including a N425K mutation are introduced via yeast homologous recombination into a pREC_SIN_HIV-1ΔEnv/URA3 vector.

In another embodiment, PCR products spanning both the gag and pol (i.e., gag/pol) coding region of a selected HIV-1 strain are introduced via yeast homologous recombination into a pRECnfl Δgag-pol/URA3 vector (e.g., pREC_exp_HIV-1 Δgag-pol/URA3). The pRECnfl-Δgag-pol/URA3 vector includes a near-full length HIV-1 genome where a yeast uracil biosynthesis (URA3) gene has replaced at least a portion of the native gag/pol HIV-1 coding sequence.

Yeast colonies containing a recombined sequence in the pREC nfl HIV-1 vectors, for example, where a URA3 gene has been replaced by the HIV-1 env encoding a N425K mutation protein sequence, gag and/or pol protein coding sequence, may be selected on plates containing a selection agent, such as CMM-Leu +5-Fluoro-1,2,3,6-Tetrahydro-2,6-Dioxo-4-Pyrimidine Carboxylic Acid (FOA). FOA is converted to the toxic substrate 5-fluorouracil by the URA3 gene product, orotidine-5'-phosphate decarboxylase. FOA-resistant yeast including the newly recombined expression construct can then be grown in yeast complete minimal medium. In one example over 95%-98% of all yeast colonies following transfection harbor vectors with the correct insert and in the correct reading frame due to highly specific recombination.

Organisms other than yeast may also be utilized to provide homologous recombination. For example, the bacterial strains TB10-pyrF287 and TB10ΔpyrF can also be used for recombination of HIV-1 envelope, gag and/or pol protein coding sequences into the pREC nfl HIV-1 plasmids. TB10ΔpyrF strain genotype is nad::Tn10/pλ-Δcro-bro tetr pyrF. TB10ΔpyrF287 strain genotype is nad::Tn10/pλ-Δcro-bro tetr pyrF287. These strains express λ bet, gam, and exo for hyper-recombination. Additionally, pyrF is the homolog to URA3. Deleting and mutating pyrF in TB10-pyrF287 and TB10λpyrF can allow URA3 plasmids to be used for selection. This will allow the same plasmids to be currently used in the yeast system to be used in the bacterial system.

Following homologous recombination, an expression construct can then be extracted and purified from the organisms providing recombination. For example, recombined pREC nfl gp120 HIV-1 vectors including the HIV-1 gp120 envelope N425K mutant, gag and/or pol protein coding sequence(s) can be purified from the entire number of yeast colonies. In some embodiments, an expression construct is extracted and purified from about 200 to greater than 1000 individual yeast colonies.

The purified expression constructs can then be transformed into bacteria (e.g., *E. coli*) for plasmid vector propagation. In an exemplary embodiment, Electrocomp TOP10 *E. coli* bacteria cells (Invitrogen) are transformed with purified recombined pREC nfl HIV-1 vectors. Plasmid DNA, once purified from the bacteria, can be stored at −80° C. until further use. In an alternative embodiment, bacterial colonies can be transformed with crude yeast extract without the purification step. In some embodiments, transformed bacterial colonies can be screened for the N425K mutation env, gag and/or pol insert and absence of the URA3 gene using well known methods.

A cell can then be transfected with the one or more expression constructs. In some embodiments, a cell is transfected with two, three, or four expression constructs each including at least one HIV-1 gp120 N425K mutation envelope protein coding sequences and/or a suitable HIV-1 backbone sequence. Methods of transfecting and expressing genes in mammalian cells are known in the art. Transducing cells with viral vectors can involve, for example, incubating vectors with cells within the viral host range under conditions and concentrations necessary to cause transduction. See, e.g., Methods in Enzymology, vol. 185, Academic Press, Inc., San Diego, Calif. (D. V. Goeddel, ed.) (1990) or M. Krieger, Gene Transfer and Expression-A Laboratory Manual, Stockton Press, New York, N.Y.; and Muzyczka (1992) Curr. Top. Microbiol. Immunol. 158: 97-129, and references cited in each. The culture of cells, including cell lines and cultured cells from tissue samples is well known in the art. Freshney (Culture of Animal Cells, a Manual of Basic Technique, Third edition Wiley-Liss, New York (1994)) provides a general guide to the culture of cells.

An expression construct for use in a method of the invention can include a vector, such as a plasmid. Suitable vectors for use in eukaryotic and prokaryotic cells are known in the art and are commercially available or readily prepared by a skilled artisan. Additional vectors can also be found, for example, in CURRENT PROTOCOLS IN MOLECULAR BIOLOGY (Ausubel, F. M., et al., eds. 2000) and Sambrook et al., "Molecular Cloning: A Laboratory Manual," 2nd ED. (1989), the teachings of which are incorporated herein by reference. In some embodiments, transformation of a cell with a reporter molecule fragment sequence can be achieved using calcium phosphate, DEAE-dextran, electroporation, cationic lipid reagents, or any other convenient technique known in the art.

In some embodiments, the expression vectors can be mammalian expression vectors including a promoter operably linked to a reporter molecule fragment expression sequence. For example, a CMV promoter-based vector can be used. Human cytomegalovirus (CMV) promoter regulatory region drives constitutive protein expression. In certain embodiments, the expression vector is a pCMV_cplt expression vector. The pCMV_cplt expression vector can be constructed by PCR-amplifying the cytomegalovirus (CMV) sequence from pcDNA3.1zeo/CAT (Invitrogen). The TOPO vector was then subjected to digestion by MLUI and BstXI to generate a CMV promoter-driven R, U5 and gag fragment. The resulting fragment is cloned back into the pcDNA3.Izeo/CAT backbone to generate the pCMV_cplt vector.

Any cell can be transfected with the vectors described herein. The cell can be human or nonhuman. The cell can be freshly isolated (i.e., primary) or derived from a short term- or long term-established cell line. In one embodiment, the first is a eukaryotic cell, where the eukaryotic cell is a cell that can be grown in culture, using standard laboratory procedures and media well known to those of skill in the art. The cell may be any cell that is not susceptible to toxic effects of chronically expressing viral proteins and that permit cell surface expression of such proteins. In some embodiments, the cell is a cell that does not express complete complementary cell surface receptors or co-receptors for the expressed HIV-1 N425K env coded protein and therefore will not undergo fusion with itself.

Exemplary biological cell lines include NIH-3T3 murine fibroblasts, quail QT6 cells, canine Cf2Th thymocytes, Mv1 Lu mink lung cells, Sf9 insect cells, primary T-cells, human T-cell lines (e.g., H-9), U-87 MG glioma, SCL1 squamous cell carcinoma cells, CEM, HeLa epithelial carcinoma, Chinese hamster ovary (CHO) cell, SF33 cell and HEK293T cell. Such cell lines are described, for example, in the Cell Line Catalog of the American Type Culture Collection (ATCC, Rockville, Md.). In one embodiment, the first cell is a HeLa epithelial carcinoma cell or a human HEK293T cell.

In one embodiment, a cell stably expresses the recombinant HIV-1 particles including the gp120 N425 mutation and secretes it from the cell. For example, a cell may comprise a coding sequence for the HIV-1 particles stably integrated into its genome in a manner such that it is expressed in the cell and directed to the cell surface where it is secreted into the surrounding media. Once secreted into the media, the recombinant HIV-1 particles can be harvested for therapeutic use or CD4i antibody generation. In some embodiments, the recombinant HIV-1 particles are harvested about 48 to about 72 hours post-transfection. Harvested the recombinant HIV-1 particles can then be purified for example, through the use of sucrose-cushion centrifugation, and then quantified for capsid/p24 content.

In some embodiments, the HIV-1 particles secreted by the cell are defective HIV-1 particles including env, gag and pol coded proteins in the correct stoichiometry and is morphologically indistinguishable from a wild type HIV-1. For example, the cloning system described herein allows for the pREC HIV-1 nfl plasmid upon 293T transfections to produce vectors that lack 5'LTR and as such cannot initiate reverse transcription, lack a functional reverse transcriptase enzyme, lack genomic RNA due to deletion of Ψ packaging element, contains full complement of HIV-1 proteins in the correct stoichmetry, and are dead but morphologically identical to wild type.

Once a nucleic acid is incorporated into a cell as provided herein, the cell can be maintained under suitable conditions for constant expression of the recombinant HIV-1 particles. Generally, the cells are maintained in a suitable buffer and/or growth medium or nutrient source for growth of the cells and expression of the gene product(s). Exemplary growth medium can include, but is not limited to, DMEM medium/ L-glutamine (GIBCO;CELLGRO;MEDIATECH) supplemented with FBS (CELLGRO), penicillin/streptomycin (GIBCO), puromycin and G418 (MEDIATECH).

As described in more detail below, the recombinant HIV-1 particles can be used to form a therapeutic composition, such as a vaccine or pharmaceutical composition. The vaccine can include a therapeutically effective amount of the replication defective recombinant HIV-1 particles including a gp120 envelope protein N425K mutation and a pharmaceutically acceptable carrier.

While it is possible that the vaccine can comprise the replication defective recombinant HIV-1 particles including a gp120 envelope protein N425K mutation in a pure or substantially pure form, it will be appreciated that the vaccine can additionally or optionally include the replication defective recombinant HIV-1 particles and a pharmaceutically acceptable carrier or other therapeutic agent. For example, the pharmaceutically acceptable carrier can include a physiologically acceptable diluent, such as sterile water or sterile isotonic saline. As used herein, the term "pharmaceutically acceptable carrier" can refer to any and all solvents, dispersion media, coatings, antibacterial and antifungal agents, isotonic and absorption delaying agents, and the like.

Additional components that may be present with the vaccine can include adjuvants, preservatives, chemical stabilizers, and/or other proteins. Typically, stabilizers, adjuvants, and preservatives are optimized to determine the best formulation for efficacy in a subject. Exemplary preservatives can include, but are not limited to, chlorobutanol, potassium sorbate, sorbic acid, sulfur dioxide, propyl gallate, the parabens, ethyl vanillin, glycerin, phenol, and parachlorophenol. Suitable stabilizing ingredients can include, for example, casamino acids, sucrose, gelatin, phenol red, N-Z amine, monopotassium diphosphate, lactose, lactalbumin hydrolysate, and dried milk. Other examples of pharmaceutically acceptable carriers are known in the art and described below.

A vaccine comprising the replication defective recombinant HIV-1 particles including a gp120 envelope protein N425K mutation can be used either prophylactically or therapeutically. When provided prophylactically, the vaccine can be provided in advance of any evidence of an active HIV infection and thereby attenuate or prevent HIV infection. For example, a human at high risk for HIV infection can be prophylactically treated with a vaccine comprising the replication defective recombinant HIV-1 particles and a pharmaceutically acceptable carrier. When provided therapeutically, the vaccine can be used to enhance a subject's own immune response to the antigens present as a result of HIV infection. It will be appreciated that the replication defective recombinant HIV-1 particles can be conjugated with one or more lipoproteins, administered in liposomal form, or with an adjuvant.

Inhibiting a viral infection can refer to inhibiting the onset of a viral infection, inhibiting an increase in an existing viral infection, or reducing the severity of the viral infection. In this regard, one of ordinary skill in the art will appreciate that while complete inhibition of the onset of a viral infection is desirable, any degree of inhibition of the onset of a viral infection is beneficial. Likewise, one of ordinary skill in the art will appreciate that while elimination of viral infection is desirable, any degree of inhibition of an increase in an existing viral infection or any degree of a reduction of a viral infection is beneficial.

Inhibition of a viral infection can be assayed by methods known in the art, such as by assessing viral load. Viral loads can be measured by methods known in the art, such as by using PCR to detect the presence of viral nucleic acids or antibody-based assays to detect the presence of viral protein in a sample (e.g., blood) from a subject. Alternatively, the number of CD4+ T cells in a viral-infected subject can be measured. A treatment that inhibits an initial or further decrease in CD4+ T cells in a viral-infected subject, or that results in an increase in the number of CD4+ T cells in a viral-infected subject, for example, may be considered an efficacious or therapeutic treatment.

Optimal dosages to be administered may be readily determined by those skilled in the art, and will vary with the particular compound used, the strength of the preparation, the mode of administration, and the advancement of the disease condition. In addition, factors associated with the particular patient being treated, including patient age, weight, diet and time of administration, will result in the need to adjust dosages.

Another aspect of the application can include a method for inducing an immune response in a subject against HIV. The method can include administering to the subject an effective amount of the replication defective recombinant HIV-1 particles encoding a gp120 envelope protein N425K mutation, wherein the HIV-1 particles elicit the immune response and thereby prevents or inhibits HIV infection in the subject. The immune response can include the generation of broadly neutralizing HIV-1 CD4 induced (CD4i) antibodies directed to the coreceptor (e.g., CCR5) binding site exposed as a result of enhanced CD4 binding to HIV-1 gp120 N425K envelope protein encoded by the vaccine particles.

In addition to the HIV-1 particles themselves, it is further contemplated that potent broadly neutralizing antibodies (bnAbs) generated by a host organism in response to HIV-1 particles encoding a gp120 envelope protein N425K mutation described herein can serve as a promising candidate for prevention and treatment of HIV-1 infection.

Thus, in some embodiments, once an HIV-1 particle vaccine encoding a N425K gp120 envelope protein is produced as described above, the vaccine can be administered to a host organism (e.g., human, mouse, monkey or rabbit) to generate broadly neutralizing CD4i antibodies directed to the coreceptor (e.g., CCR5) binding site exposed as a result of enhanced CD4 binding to HIV-1 N425K gp120 envelope protein. Normally these epitopes are poorly presented in the host due to short and labile transitional states of the CD4i complex (i.e., after gp120-CD4 binding and prior to interactions with the co-receptor (CCR5 or CXCR4). Thus, another aspect of the application can include a method for generating broadly neutralizing CD4i antibodies targeting the CD4 induced (CD4i) confirmation of gp120.

In an exemplary embodiment, mice are vaccinated with a dSHIVsimian/human immunodeficiency virus envelope protein encoding vector including the N425K mutation using a prime-boost strategy. Mice can be vaccinated either with or without the additional administration of an adjuvant. Blood is then collected to isolate sera for measuring neutralizing antibody (Nab) activity of the generated antibodies. In an exemplary embodiment, huCD4-B mice (transgenic mice with human CD4+ B cells) are immunized with a deactivated SHIVEnvA$_{N425K}$ vaccine construct at a dose of $10^7$ TCID$_{50}$ per immunization in 100 ul of media. Animals can be boosted twice every two week. Blood can be sampled from tail veins.

In certain embodiments, B cells can be purified from the spleens of sacrificed vaccinated animals to generate hybridomas producing a selected antibody using well known methods. The generation of hybridomas can allow for rapid screening and for the production of Nabs directed to the CD4 coreceptor binding site. For example, an isolated CD4+ B cell producing a selected CD4i antibody can be fused with an immortal cell to create a hybridoma cell capable of producing an identified broadly neutralizing CD4i antibody.

Neutralizing CD4i Abs produced as described herein can be identified through the use of a select panel of HIV viruses and/or B cell hybridoma screening approaches described in the Example section below. In some embodiments, broadly neutralizing CD4i Abs can be identified through the use of an Affinofile system used to screen for CD4i sensitivity. For example, 293 cells in the Affinofile are adjusted to express high CD4 (40,000/cell) and low CCR5 (2,500/cell) and then utilized in Nab assays with various generated CD4i neutralizing Abs. In some embodiments, an ELISA screening can be used to detect and identify Nabs. In an exemplary embodiment, an ELISA screening can include N425K rgp 120-coated plates.

In some embodiments, a pharmaceutical composition administered to a subject includes a therapeutically effective amount of the replication defective recombinant HIV-1 particles and/or broadly neutralizing CD4i antibodies described herein, and another therapeutic agent useful in the treatment of HIV infection, such as a component used for HAART or immunotoxins.

As noted above, compositions described herein may be combined with one or more additional therapeutic agents useful in the treatment of HIV infection. It will be understood that the scope of combinations of the compounds of this invention with HIV/AIDS antivirals, immunomodulators, anti-infectives or vaccines is not limited to the following list, and includes in principle any combination with any pharmaceutical composition useful for the treatment of AIDS. The HIV/AIDS antivirals and other agents will typically be employed in these combinations in their conventional dosage ranges and regimens as reported in the art.

Examples of antiviral agents include (but not restricted) ANTIVIRALS Manufacturer (Trade name and/or Drug Name Location) Indication (Activity): abacavir GlaxoSmithKline HIV infection, AIDS, ARC GW 1592 (ZIAGEN) (nRTI); 1592U89 abacavir+GlaxoSmithKline HIV infection, AIDS, ARC (nnRTI); lamivudine+(TRIZIVIR) zidovudine acemannan Carrington Labs ARC (Irving, Tex.) ACH 126443 Achillion Pharm. HIV infections, AIDS, ARC (nucleoside reverse transcriptase inhibitor); acyclovir Burroughs Wellcome HIV infection, AIDS, ARC, in combination with AZT AD-439 Tanox Biosystems HIV infection, AIDS, ARC AD-519 Tanox Biosystems HIV infection, AIDS, ARC adefovir dipivoxil Gilead HIV infection, AIDS, ARC GS 840 (RTI); AL-721 Ethigen ARC, PGL, HIV positive, (Los Angeles, Calif.), AIDS alpha interferon GlaxoSmithKline Kaposi's sarcoma, HIV, in combination w/Retrovir AMD3100 AnorMed HIV infection, AIDS, ARC (CXCR4 antagonist); amprenavir GlaxoSmithKline HIV infection, AIDS, 141 W94 (AGENERASE) ARC (PI); GW 141 VX478 (Vertex) ansamycin Adria Laboratories ARC LM 427 (Dublin, Ohio) Erbamont (Stamford, Conn.) antibody which neutralizes; Advanced Biotherapy AIDS, ARC pH labile alpha aberrant Concepts (Rockville, Interferon Md.) AR177 Aronex Pharm HIV infection, AIDS, ARC atazanavir (BMS 232632) Bristol-Myers-Squibb HIV infection, AIDS, ARC (ZRIVADA) (PI); beta-fluoro-ddA Nat'l Cancer Institute AIDS-associated diseases BMS-232623 Bristol-Myers Squibb/HIV infection, AIDS, (CGP-73547) Novartis ARC (PI); BMS-234475 Bristol-Myers Squibb/HIV infection, AIDS, (CGP-61755) Novartis ARC (PI); capravirine Pfizer HIV infection, AIDS, (AG-1549, S-1153) ARC (nnRTI); CI-1012 Warner-Lambert HIV-1 infection cidofovir Gilead Science CMV retinitis, herpes, papillomavirus curdlan sulfate AJI Pharma USA HIV infection cytomegalovirus immune MedImmune CMV retinitis globin cytovene Syntex sight threatening CMV ganciclovir peripheral CMV retinitis delavirdine Pharmacia-Upjohn HIV infection, AIDS, (RESCRIPTOR) ARC (nnRTI); dextran Sulfate Ueno Fine Chem. Ind. AIDS, ARC, HIV Ltd. (Osaka, Japan) positive asymptomatic ddC Hoffman-La Roche HIV infection, AIDS, ARC (zalcitabine, (HIVID) (nRTI); dideoxycytidine ddI Bristol-Myers Squibb HIV infection, AIDS, ARC; Dideoxyinosine (VIDEX) combination with AZT/d4T (nRTI) DPC 681 & DPC 684 DuPont HIV infection, AIDS, ARC (PI) DPC 961 & DPC 083 DuPont HIV infection AIDS, ARC (nnRTRI); emvirine Triangle Pharmaceuticals HIV infection, AIDS, ARC (CO-ACTINON) (non-nucleoside reverse transcriptase inhibitor); EL10 Elan Corp, PLC HIV infection (Gainesville, Ga.) efavirenz DuPont HIV infection, AIDS, (DMP 266) (SUSTIVA) ARC (nnRTI); Merck (STOCRIN) famciclovir Smith Kline herpes zoster, herpes simplex emtricitabine Triangle Pharmaceuticals HIV infection, AIDS, ARC FTC (CO- VIRACIL) (nRTI); Emory University emvirine Triangle Pharmaceuticals HIV infection, AIDS, ARC (COACTINON) (non-nucleoside reverse transcriptase inhibitor); HBY097 Hoechst Marion Roussel HIV infection, AIDS, ARC (nnRTI); hypericin VIMRx Pharm. HIV infection, AIDS, ARC recombinant human; Triton Biosciences AIDS, Kaposi's sarcoma, interferon beta (Almeda, Calif.); ARC interferon alfa-n3 Interferon Sciences ARC, AIDS indinavir; Merck (CRIXIVAN) HIV infection, AIDS, ARC, asymptomatic HIV positive, also in combination with AZT/ddI/ddC (PI); ISIS 2922 ISIS Pharmaceuticals CMV retinitis JE2147/AG1776; Agouron HIV infection, AIDS, ARC (PI); KNI-272 Nat'l Cancer Institute HIV-assoc. diseases lamivudine; 3TC Glaxo Wellcome HIV infection, AIDS, (EPIVIR) ARC; also with AZT (nRTI); lobucavir Bristol-Myers Squibb CMV infection; lopinavir (ABT-378) Abbott HIV infection, AIDS, ARC (PI); lopinavir+ritonavir Abbott (KALETRA) HIV infection, AIDS, ARC (ABT-378/r) (PI); mozenavir AVID (Camden, N.J.) HIV infection, AIDS, ARC (DMP-450) (PI); nelfinavir Agouron HIV infection, AIDS, (VIRACEPT) ARC (PI); nevirapine Boeheringer HIV infection, AIDS, Ingleheim ARC (nnRTI); (VIRAMUNE) novapren Novaferon Labs, Inc. HIV inhibitor (Akron, Ohio); pentafusaide Trimeris HIV infection, AIDS, ARC T-20 (fusion inhibitor); peptide T Peninsula Labs AIDS octapeptide (Belmont, Calif.) sequence PRO 542 Progenics HIV infection, AIDS, ARC (attachment inhibitor); PRO 140 Progenics HIV infection, AIDS, ARC (CCR5 co-receptor inhibitor); trisodium Astra Pharm. Products, CMV retinitis, HIV infection, phosphonoformate Inc other CMV infections; PNU-140690 Pharmacia Upjohn HIV infection, AIDS, ARC (PI); probucol Vyrex HIV infection, AIDS; RBC-CD4Sheffield Med. Tech HIV infection, AIDS, (Houston Tex.) ARC; ritonavir Abbott HIV infection, AIDS, (ABT-538) (RITONAVIR) ARC (PI); saquinavir Hoffmann-LaRoche HIV infection, AIDS, (FORTOVASE) ARC (PI); stavudine d4T Bristol-Myers Squibb HIV infection, AIDS, ARC didehydrodeoxy-(ZERIT.) (nRTI); thymidine T-1249 Trimeris HIV infection, AIDS, ARC (fusion inhibitor); TAK-779 Takeda HIV infection, AIDS, ARC (injectable CCR5 receptor antagonist); tenofovir Gilead (VIREAD) HIV infection, AIDS, ARC (nRTI); tipranavir (PNU-140690) Boehringer Ingelheim HIV infection, AIDS, ARC (PI); TMC-120 & TMC-125 Tibotec HIV infections, AIDS, ARC (nnRTI); TMC-126 Tibotec HIV infection, AIDS, ARC (PI); valaciclovir GlaxoSmithKline genital HSV & CMV infections virazole Viratek/ICN (Costa asymptomatic HIV positive, ribavirin Mesa, Calif.) LAS, ARC; zidovudine; AZT GlaxoSmithKline HIV infection, AIDS, ARC, (RETROVIR) Kaposi's sarcoma in combination with other therapies (nRTI); [PI=protease inhibitor nnRTI=non-nucleoside reverse transcriptase inhibitor NRTI=nucleoside reverse transcriptase inhibitor].

The additional therapeutic agent may be used individually, sequentially, or in combination with one or more other such therapeutic agents described herein. Administration to a subject may be by the same or different route of administration or together in the same pharmaceutical formulation.

According to this embodiment, a composition comprising the replication defective recombinant HIV-1 particles may be coadministered with any HAART regimen or component thereof. The current standard of care using HAART is usually a combination of at least three nucleoside reverse transcriptase inhibitors and frequently includes a protease inhibitor, or alternatively a non-nucleoside reverse transcriptase inhibitor. Subjects who have low $CD4^+$ cell counts or high plasma RNA levels may require more aggressive HAART. For subjects with relatively normal $CD4^+$ cell counts and low to non-measurable levels of plasma HIV RNA over prolonged periods (i.e., slow or non-progressors) may require less aggressive HAART. For antiretroviral-naive subject who are treated with initial antiretroviral regimen, different combinations (or cocktails) of antiretroviral drugs can be used.

Thus, in some embodiments, a pharmaceutical composition comprising the replication defective recombinant HIV-1 particles encoding a gp120 envelope protein having an N425K mutation may be coadministered to the subject with a "cocktail" of nucleoside reverse transcriptase inhibitors, non-nucleoside HIV reverse transcriptase inhibitors, and protease inhibitors. For example, a pharmaceutical composition including the replication defective recombinant HIV-1 particles and an HDAC inhibitor may be coadministered with a cocktail of two nucleoside reverse transcriptase inhibitors (e.g., ZIDOVUDINE (AZT) and LAMIVUDINE (3TC)), and one protease inhibitor (e.g., INDINAVIR (MK-639)).

Coadministration in the context of this invention is defined to mean the administration of more than one therapeutic agent in the course of a coordinated treatment to achieve an improved clinical outcome. Such coadministration may also be coextensive, that is, occurring during overlapping periods of time.

Pharmaceutical compositions described herein can be formulated by standard techniques using one or more physiologically acceptable carriers or excipients. Suitable pharmaceutical carriers are described herein and in "Remington's Pharmaceutical Sciences" by E. W. Martin. The small molecule compounds of the present invention and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablets or a capsule prepared by conventional means with a pharmaceutically acceptable excipient. Preferred are tablets and gelatin capsules comprising the active ingredient, i.e., a small molecule compound of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds described herein can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In one embodiment, a pharmaceutical composition is administered to a subject, preferably a human, at a therapeutically or immunologically effective dose to prevent, treat, or control a condition or disease as described herein, such as HIV.

The dosage of active compounds administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular small molecule compound in a particular subject. Typically, a dosage of the active compounds of the present invention is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

In another embodiment, a pharmaceutical composition including the replication defective recombinant HIV-1 particles is administered in a daily dose in the range from about 0.1 mg per kg of subject weight (0.1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In yet another embodiment, the daily dose is about 25 mg/kg to about 150 mg/kg. A preferred dose is about 10 mg/kg. The daily dose can be administered once per day or divided into subdoses and administered in multiple doses, e.g., twice, three times, or four times per day.

To achieve the desired therapeutic effect, compositions described herein may be administered for multiple days at the therapeutically effective daily dose. Thus, therapeutically effective administration of compounds to treat a condition or disease described herein in a subject requires periodic (e.g., daily) administration that continues for a period ranging from three days to two weeks or longer. Typically, compounds will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, one can administer the compounds every other day, every third day, or, if higher dose ranges are employed and tolerated by the subject, once a week. A preferred dosing schedule, for example, is administering daily for a week, one week off and repeating this cycle dosing schedule for 3-4 cycles.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$ Compounds that exhibit large therapeutic indices are preferred. While compounds that exhibit toxic side effects can be used, care should be taken to design a delivery system that targets such compounds to the HIV infected cells to minimize potential damage to normal cells and, thereby, reduce side effects. In addition, combinations of compounds having synergistic effects described herein can be used to further reduce toxic side effects of one or more agents comprising a pharmaceutical composition of the invention.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Following successful treatment, it may be desirable to have the subject undergo maintenance therapy to prevent the recurrence of the condition or disease treated.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

Example 1

Maraviroc is an imidazopyridine that binds a hydrophobic transmembrane cavity of CCR5, altering the conformation of the extracellular loops of the receptor and disrupting chemokine binding as well as interactions with the gp120 envelope glycoprotein. In this Example we show the isolation of MVC resistant variants from a subtype A HIV-1 primary isolate which developed resistance over 21 weeks of tissue culture passage in the presence of dose escalations of inhibitor. Resistance in this virus appeared to map to a mutation in the C4 region of gp120. Drug sensitivity assays of gp120 chimeric virus clones derived from the resistant virus did not display reductions in maximal percent inhibition (MPI) but rather showed increases in $IC_{50}$ values up to 40-fold compared to the parental virus. These pronounced shifts in $IC_{50}$ value as well as the location of the primary resistance mutation in structural modeling predictions shows a novel MVC resistance mechanism related to altered CD4 binding.

Materials and Methods

Cells, Viruses, and Inhibitors

U87.CD4.CCR5 cells were obtained through the AIDS Research and Reference Reagent Program, Division of AIDS, NIAID, NIH. U87.CD4.CCR5 cells were maintained in DMEM supplemented with 10% FBS, 100 μg/mL penicillin/streptomycin, 300 μg/mL G418, and 1 μg/mL puromycin (Invitrogen, Carlsbad, Calif.). 293T cells were cultured in DMEM supplemented with 10% FBS and 100 μg/mL penicillin/streptomycin. Peripheral blood mononuclear cells (PBMCs) were obtained from whole blood extracted from a HIV negative donor by Ficoll-Paque centrifugation. PBMC cultures were stimulated with 1 μg/mL phytohemagglutinin (PHA; Gibco, Carlsbad, Calif.) for 48 hrs in RPMI 1640 medium (Gibco) containing 10% FBS and 100 μg/mL penicillin/streptomycin. Cells were maintained thereafter in RPMI 1640 medium with 10% FBS, 100 μg/mL penicillin/streptomycin, and 10,000 U/mL interleukin-2 (IL-2; Gibco).

HIV-1 primary isolates $(B6)_{91US715}$ and $(C8)_{96USNG58}$ were obtained from the National Institutes of Health AIDS Research and Reference Reagent Program while virus A74 was isolated from a Ugandan patient through the Center for AIDS Research core facility in Kampala, Uganda. Viral swarms were propagated in U87.CD4.CCR5 cells and titers were determined by the Reed-Muench endpoint titration method.

Maraviroc (MVC) and TAK-779 were diluted in PBS while enfuvirtide (T20) was diluted in ethanol.

Resistant Virus Isolation

Three viruses (A74, B6, and C8) were propagated on U87.CD4.CCR5 cells in a 6-well plate format ($1.5\times10^5$ cells/well) using an initiating inoculum of virus (0.001 IU/cell) in either the presence or absence of MVC. Inhibitor concentration was increased when viral replication was detected using a radio-labeled reverse transcriptase assay as previously described. Equivalent volumes of supernatant (50-100 μL) were passaged onto fresh U87.CD4.CCR5 cells either with or without inhibitor each week. Weekly supernatants were collected and frozen.

Multiple Replication Cycle Drug Susceptibility Assays

U87.CD4.CCR5 cells were plated in 96-well format ($1\times10^4$ cells/well) for 24 hr. Cells were then treated for 2 hr with 5-fold dilutions of MVC (100 μM to $2\times10^{-6}$ μM) and then infected at a multiplicity of infection (MOI) of 0.001 infectious units (IU)/cell. All assays were performed in triplicate. After 24 hr, cells were washed in 1×PBS to remove free virus and media containing the appropriate MVC drug dilutions was added. Viral replication was measured daily by radio-labeled reverse transcriptase assay using a Packard beta counter to quantify counts per minute (cpm). Drug sensitivity curves were generated using non-linear regression curve fitting features of GraphPad Prism 5 software.

Construction of gp120 Chimeric Viruses

Gp120 chimeric viruses were cloned into an NL4-3 backbone from passage control and virus passaged in the presence of MVC escalations using the yeast homologous recombination-gap repair technique. From this point forward, the viruses and clones are referred to as PG (passage control) or MVC (maraviroc selected). 21 (number of passages). 1 (clone number) or PC.21.1 or MVC.21.1. The gp120 regions of the PC.1 (starting virus), PC.21 and MVC.21 viruses were PCR amplified using primers F_gp120 5'-GACAGGTTAATTGATAGACTA-3' (SEQ ID NO: 1) and B_gp120 5'-CTTCCTGCTGCTCCCAAGAAC-3' (SEQ ID NO: 2). Briefly, these gp120 PCR products were then co-transformed with a SacI-linearized pREC_NFL_Δgp120/URA3 into *Saccharomyces cerevisiae* MYA-906 cells (ATCC). Following homologous recombination, plasmids were extracted from the yeast cells and transformed into electrocompetent *Escherichia coli* Stbl4 cells (Invitrogen). Individual bacterial colonies were grown and plasmids were extracted using Qiagen miniprep kits. Chimeric pREC_NFL_gp120 plasmids were co-transfected into 293T cells ($3\times10^4$ cells/well) along with the complementing plasmid pCMV_cplt using Fugene 6 reagent (Promega, Madison, Wis.) as described. Heterodiploid virus particles containing one copy of the NFL and cplt HIV-1 RNAs represent approximately half of the virus derived from 293T cell transfections and can be propagated on U87.CD4.CCR5 cells to produce replication competent virus with a complete virus genome. Virus stocks of each clone were titered as described above. The DNA sequences obtained in the course of this work were deposited in the GenBank/EMBL/DDBJ databases under the following accession numbers: env(gp120) (JX993942-JX993981).

Oligonucleotide Ligation Assay

The gp120 regions of the bulk passage control (PC.21) and resistant virus (MVC.21) were RT-PCR amplified using envend 5'-CTTTTTGACCACTTGCCACCCAT-3' SEQ ID NO: 3) for reverse transcription and F_gp120/B_gp120 for subsequent PCR amplification. Oligonucleotides were designed for ligase discrimination reactions to bind upstream or downstream of the mutation sites observed in MVC.21 for envelope codons 117, 396, and 425. For each mutation site, we employed two upstream interrogator oligonucleotides to discriminate between and quantify the sequences $R_{CGA}$ and $Q_{CAA}$ at codon 117, sequences $L_{TTA}$, $G_{GGA}$, $V_{GTA}$ at codon 396 and sequences $N_{AAT}$ and $K_{AAA}$ at codon 425. A complete description of this ligase discrimination assay has been described previously.

Site-Directed Mutagenesis PCR Method

The K425 mutation was introduced into the MVC.21.122 gp120 clone by a nested PCR amplification method. Two PCR fragments were generated from the pREC_N-FL_gp120/MVC.21.122 plasmid using primers F_gp120 with B_K425 5'-CTACTCTTTGCCACATCTTTATAAT-TTGCTTTATTCTGCATGGAAGA-3' (SEQ ID NO: 4) and F_K425 5'-TCTTCCATGCAGAATAAAGCAAATTATA-AAGATGTGGCAAAGAGTAG-3' SEQ ID NO: 5) with B_gp120. Using products from these PCR amplifications as templates, a nested PCR was performed with primers F_gp120 and B_gp120 to generate the full gp120 region which was subsequently cloned into pREC_NFL_Δgp120/URA3 by yeast homologous recombination as described above. Individual colonies were sequenced and a single clone containing the K425 mutation was identified and named pREC_NFL_gp120/MVC.21.122.425K. Replication competent virus was generated from this plasmid by co-transfection in 293T cells and propagation in U87.CD4.CCR5 cells as described above.

In Vitro Fitness Assays

The replicative fitness of PC.21 and MVC.21 gp120 chimeric viruses were assessed in head to head competition experiments in U87.CD4.CCR5 cells as described in. Cells were plated in 48-well format ($2\times10_5$ cells/well) and infected in triplicate with viruses at an MOI of 0.0001 IU/mL. Infected cells were collected five days post infection and genomic DNA was isolated using Qiagen kit. The gp120 region was amplified from cellular DNA using F_gp120/B_gp120 as described earlier. Amplicons were probed for sequence identity at gp120 residue 117 and 425 OLA. Frequency of wild type or mutant residue identity versus total signal was used to determine viral fitness. Fitness difference ($W_D$) was calculated as the fitness of the resistant virus divided by the fitness of the sensitive virus.

Structural Modeling

The structural model of N425K mutant was generated from the crystal structure of gp120 in complex with CD4 and a tyrosine-sulfated antibody 412d (PDB ID:2QAD). The mutation of N425 to K425 was made in the model building program COOT and the local structure around the mutation was regularized using the same program. By a slight torsion of the K425 side chain, two close contacts can be made from the Nε of K425 with residues from CD4 including a cation-π interaction with F43 of CD4.

Results

Maraviroc Resistant Mutant Generated in Cell Culture

The concentration of entry inhibitor required to inhibit viral replication by 50% ($IC_{50}$) can vary up to 1000 fold when comparing HIV-1 primary isolates that have never been exposed to these drugs. We assessed "intrinsic" susceptibilities of HIV-1 subtype A, B, and C primary isolates to maraviroc. Multiple cycle drug susceptibility assays were performed in U87.CD4.CCR5 cells in the presence of 5-fold decreasing concentrations of MVC starting at 100 μM. The subtype A primary isolate (A74) was less sensitive to MVC inhibition ($IC_{50}$=10 nM) compared with the subtype B (B6) and C (C8) viruses which had similar sensitivity (mean $IC_{50}$=2 nM) (FIG. 1A).

Given the differential sensitivity to MVC, these three primary isolates were passaged weekly in the presence of increasing MVC concentrations in U87 human glioma cells expressing CD4 and CCR5 to generate a maraviroc escape mutant (FIG. 1B). As a control, viruses were also passaged in the absence of inhibitor to differentiate changes that occurred as a result of drug pressure versus selection during long term culture. Reverse transcriptase (RT) activity was monitored in the cell-free supernatant for each weekly passage and inhibitor concentration increased when RT activity reached 2-fold over background. Virus C8 cultures were abandoned after failure to produce robust RT activity in weeks 15 and 16. Although virus B6 cultures continued to produce RT activity through week 21, viruses collected from this passage remained sensitive to MVC with $IC_{50}$ values for control and inhibitor treated cultures 8 nM and 14 nM, respectively (Table 1).

Figure 2:
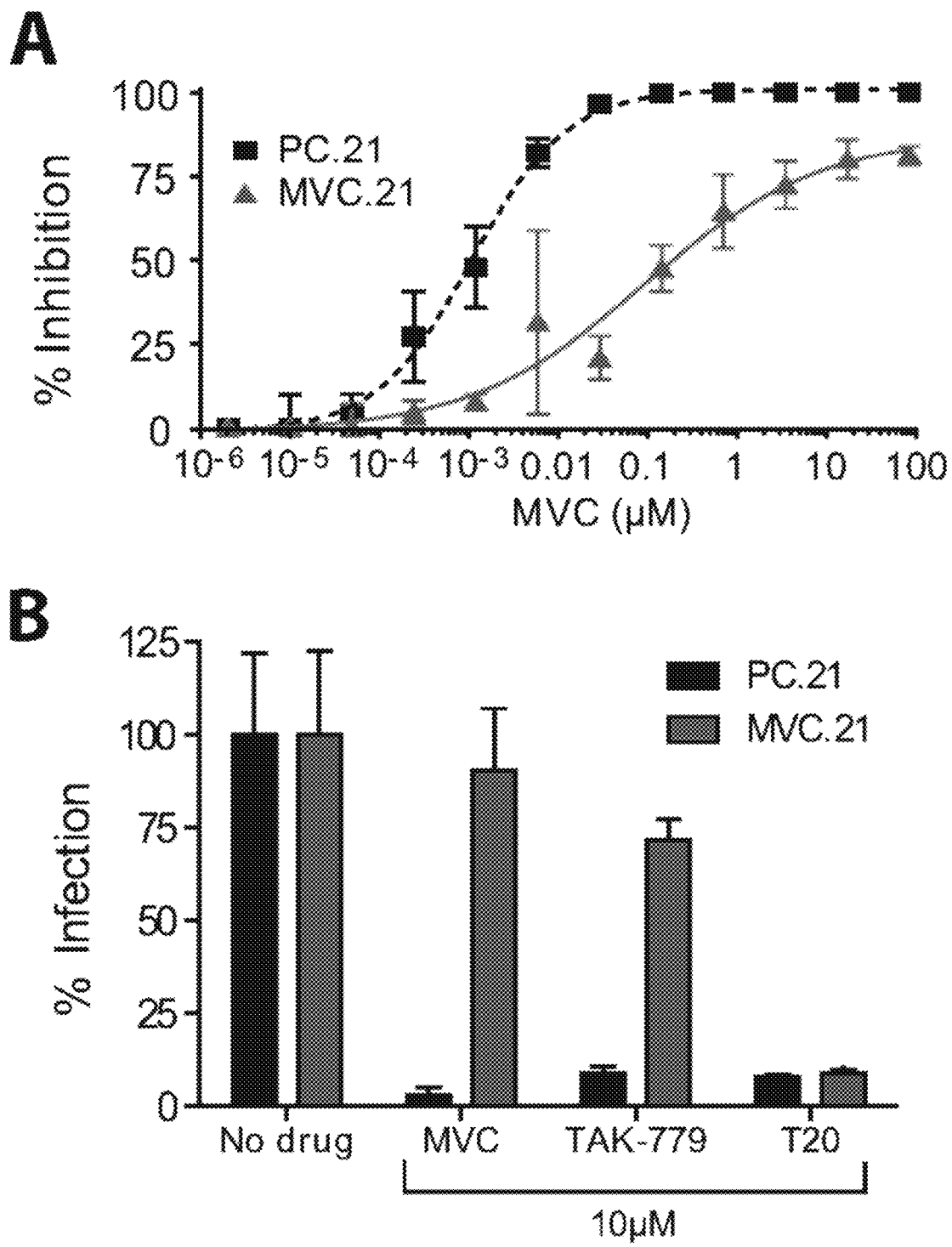
FIGS. 2(A-B) illustrate a plot and graph showing MVC resistance and cross resistance to TAK-779 after prolonged culture with MVC inhibitor. (A) Virus A74 derived from passage control week 21 (PC.21) and MVC treated week 21 (MVC.21) cultures were used to infect U87.CD4.CCR5 cells in the presence of increasing concentrations of MVC. (B) These viruses were also used to infect U87.CD4.CCR5 cells in the presence of maximal inhibitory concentrations (10 µM) of CCR5 antagonists MVC and TAK-779 and fusion inhibitor enfuvirtide (T20). Reverse transcriptase activity was measured 7 days post infection. Percent infection was calculated relative to the no drug control for each virus. Data shown are means of triplicates with error bars representing standard deviations.

Drug susceptibility analyses of virus A74 at week 21 (MVC.21) in U87.CD4.CCR5 cells indicated this virus was able to escape inhibition by MVC at concentrations >1,000 fold higher than the $IC_{50}$ value for the input virus (FIG. 2A). At the highest drug concentration tested (100 μM), MVC.21 was inhibited by 81%, indicating incomplete suppression of virus entry despite saturating levels of inhibitor. In addition to this reduction in the maximal percent inhibition (MPI), a shift in $IC_{50}$ value to 216 nM was also observed for MVC.21 virus representing a 20-fold level in resistance compared to the inoculating virus. In contrast, the passage control virus (PC.21) demonstrated a slight hypersensitivity to MVC with an $IC_{50}$ of 1 nM. While the use of cells lacking CXCR4 made a switch in coreceptor usage unlikely, tropism testing performed in U87.CD4.CXCR4 cells confirmed no dual or X4-tropic viruses arose during the 21 passages (data not shown).

The U87 human glioma cell line is stably transfected to express high levels of CD4 and CCR5 which does not accurately reflect levels on natural HIV-1 targets, e.g. CD4+ T cells and macrophages. Therefore, multiple cycle drug sensitivity assays were performed in peripheral blood mononuclear cells (PBMC) isolated from an HIV negative donor with PC.21 and MVC.21. The results confirmed those observed in the U87.CD4.CCR5 cells with a reduction in MPI of MVC.21 to 73% and an $IC_{50}$ value of 300 nM compared to 5 nM for PC.21 (Table 1).

TABLE 1

| Virus | U87.CD4.CCR5 | | PBMC | |
|---|---|---|---|---|
| | IC50 (nm) | MPI % | IC50 (nM) | MPI (%) |
| A74 | 10 | 99 | 5 | 100 |
| PC.21 | 1 | 100 | 6 | 98 |
| MVC.21 | 216 | 81 | 300 | 73 |
| B6.PC.21 | 8 | 100 | ND[a] | ND |
| B6.MVC.21 | 14 | 99 | ND | ND |

MVC.21 Cross Resistant to Another CCR5 Antagonist

MVC.21 showed evidence of cross resistance to another CCR5 antagonist, TAK-779, as indicated by replication in U87.CD4.CCR5 cells treated with an $IC_{99}$ inhibitory concentration (10 μM) that completely blocked PC.21 virus replication (FIG. 2B). TAK-779 (as well as VCV and APL) has been shown to bind a similar CCR5 transmembrane region as maraviroc and likewise alter coreceptor conformation. Cross resistance to TAK-779 would suggest a mechanism of resistance that permits this virus to overcome inhibition by multiple inhibitors in this class. In contrast, 10 μM of enfuvirtide ($IC_{99}$ concentration) mediated similar levels of MVC.21 and PC.21 inhibition in U87.CD4.CCR5 cells. As a fusion inhibitor, enfuvirtide or T20 inhibits entry by targeting formation of the six helix gp41 bundle and subsequent membrane fusion. Lack of enfuvirtide resistance suggests MVC resistance in MVC.21 virus is mediated by a mechanism that precedes membrane fusion and likely relates to receptor interactions.

Multiple Mutations Throughout gp120 in Resistant Virus

Figure 3:
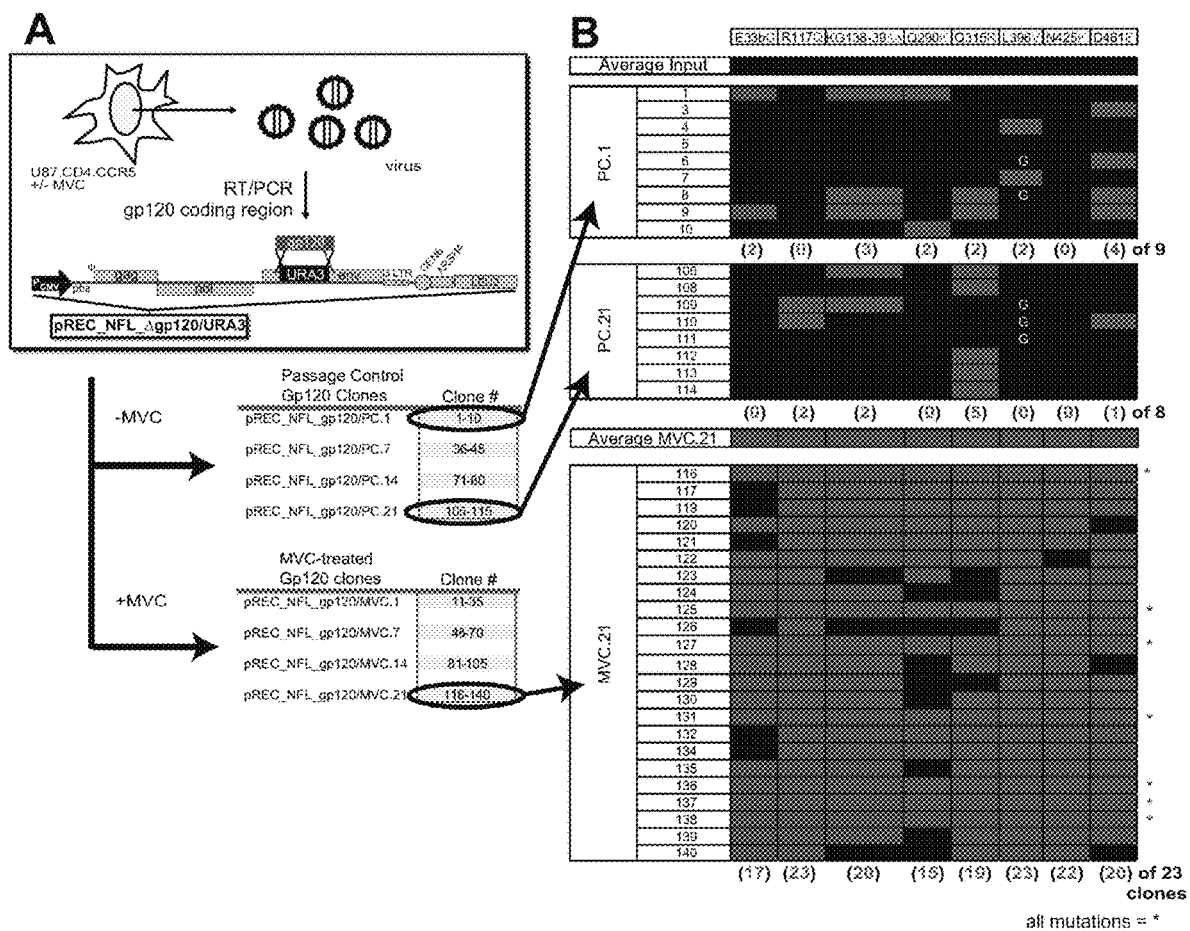
FIGS. 3(A-B) illustrate schematics showing the generation and characterization of gp120 chimeric virus. (A) Viral RNA was isolated from indicated passage control and MVC treated culture supernatants and the gp120 regions amplified after reverse transcriptase and nested PCR. Gp120 regions were recombined into pREC_NFL_Δgp120/URA3 vector using yeast homologous recombination method as described in Materials and Methods. Individual bacterial colonies were selected as indicated in the table. (B) Full gp120 regions of clones from PC.1, PC.21 and MVC.21 were sequenced. Nine mutations were identified in MVC.21 clones and are indicated based on HXB2 reference virus numbering. Rows refer to individual gp120 clones while columns refer to specific gp120 mutations. The asterisks (*) in (B) refer to clones harboring only mutations selected primarily in the MVC passage. Number of clones harboring mutations at specific gp120 sites are indicated below columns.

Population sequencing of the envelope region of the PC.21 and MVC.21 viruses identified several amino acid substitutions related to MVC selection in the gp120 region but none in gp41. To identify specific mutations and linkage in gp120 related to MVC resistance, the gp120 region of the input (PC.1), passage control (PC.21) and MVC treated virus from passages 7, 14 and 21 were PCR amplified from viral cDNA and cloned into the pREC_NFL_Δgp120/URA3 construct by yeast homologous recombination/gap repair (FIG. 3A).

Approximately 10 clones from each passage control (PC.1, PC week 7 or PC.7, PC.14, PC.21) and 25 clones from each MVC treated passage (MVC week 7 or MVC.7, MVC.14, MVC.21) were sequenced to identify mutations (>140 clones) to determine the linked amino acids selected under MVC pressure. Nine gp120 amino acid substitutions were more prevalent in the MVC.21 clones than in the PC.1 and PC.21 clones (FIG. 3B). FIG. 3B employs system where a black box at a specific position indicates the predominate/average amino acid in the inoculum virus (PC.1) while a grey box represents the predominate/average sequence in the MVC-treated virus (MVC.21). A total of twenty-three unique mutational patterns were identified based on this average sequence analyses. Some "mutant" amino acids (FIG. 3B) were observed in PC.1 and PC.21 clones and likewise, some wild type amino acids in the MVC.21 clones. Overall, the linkage pattern of these mutations in the MVC.21 population was complex with only six of twenty-three clones (FIG. 3B) having all nine mutations. Only one of nine clones in the input or PC.1 virus had wild type amino acids at all nine positions.

Figure 4:
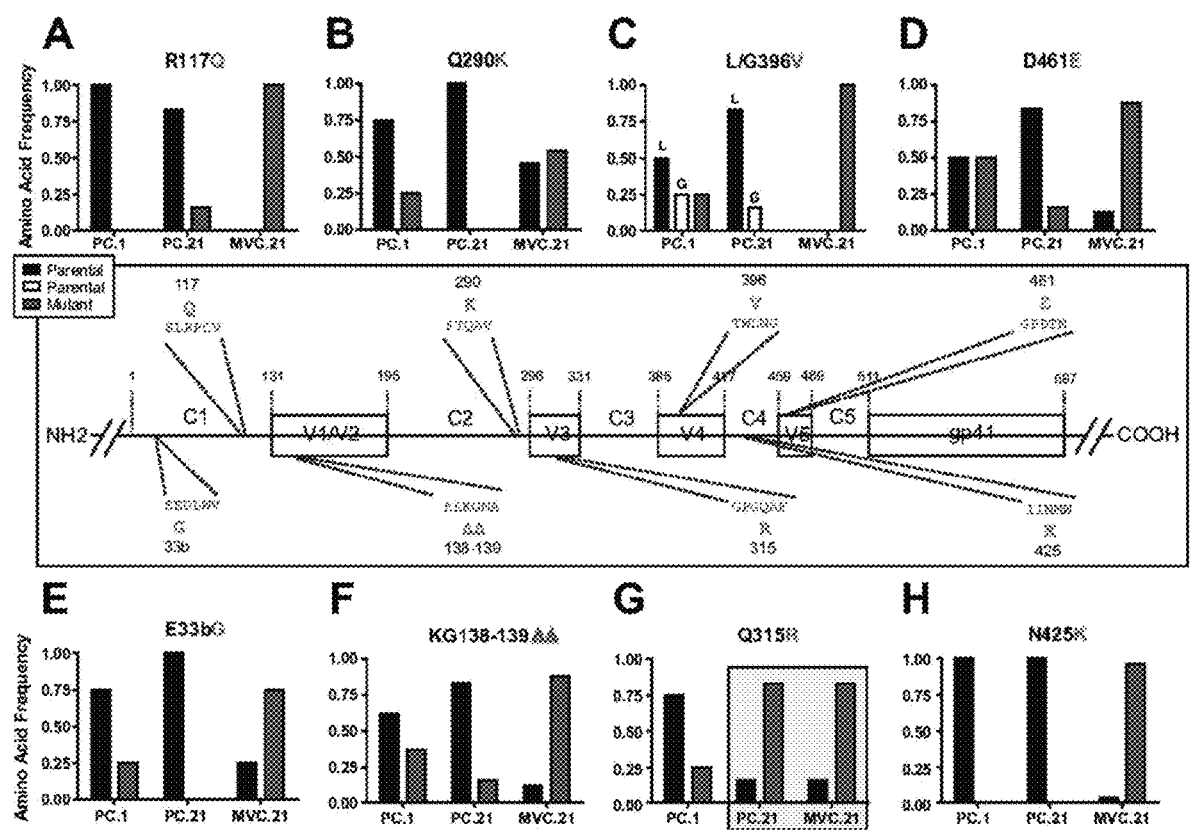
FIGS. 4(A-H) illustrate graphs showing the frequency of gp120 mutations in PC.21 and MVC.21 derived clones. The frequency of wild type and mutant amino acid are displayed and represent those individual mutations in the clones derived from PC.1, PC.21 and MVC.21 cultures. Frequencies were calculated based on number of clones with either wild type or mutant residues versus the total number of clones sequenced for that population as shown in FIG. 3B. The center panel of HIV-1 envelope gene maps the location of each mutation in gp120 conserved (C1-05) or variable (V1-V5) regions.
Figure 5:
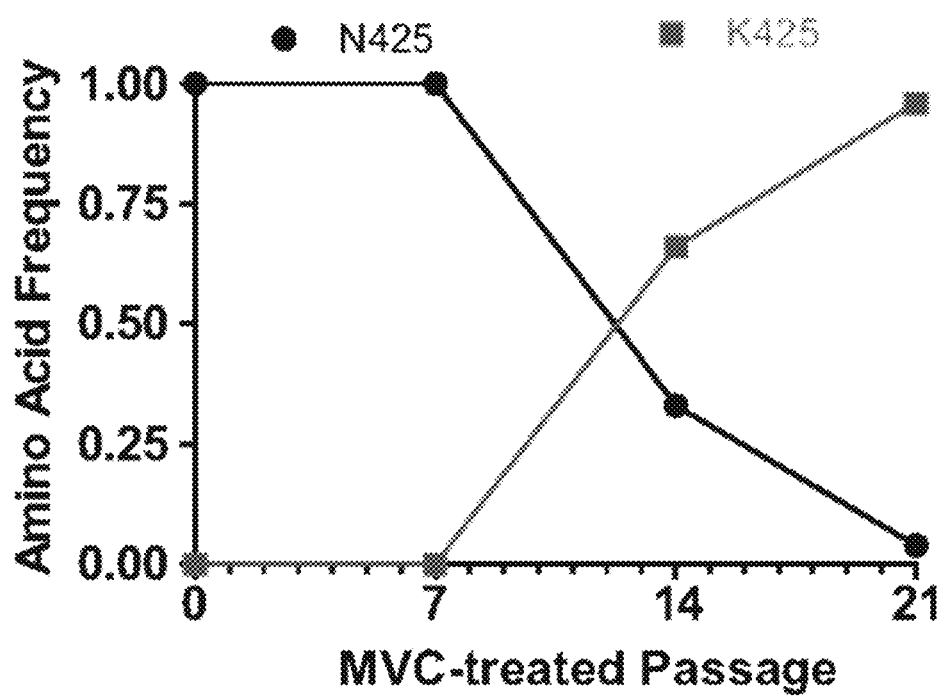
FIG. 5 illustrates a plot showing the change of gp120 mutation frequency during passage control and MVC selection. Using the clonal sequences (n=79) from the inoculum and MVC treated passage 7, 14, and 21, the frequency of N425 and K425 was determined.

The frequencies of the wild type versus mutant residues at these individual mutation sites were determined using the total number of sequenced clones. Three mutations (R117Q, L/G396V, and N425K) were found at high frequency in the MVC.21 clones but at low frequency in either the input or PC.21 clones (FIG. 4A, C, H, respectively) suggesting their role in MVC resistance. The V3 mutation Q315R was present at the same frequency in the PC.21 clones as the MVC.21 clones (FIG. 4G) suggesting this mutation emerged with normal adaptation to U87.CD4.CCR5 tissue culture and not selected under drug pressure. The remaining mutations E33bG, KG138-3944, Q290K, and D461E appeared at high frequency in the MVC.21 clones but were also found at frequencies >25% in the input population (FIG. 4E, F, B, D, respectively). In regards to linkage, the R117Q, L396V and N425K were found together in twenty-two of twenty-three MVC.21 clones but never linked in the PC.1 or PC.21 virus. The N425K mutation was found in all but one of the twenty-three MVC.21 clones (except MVC.21.122) but was absent from all seventeen of the PC.1 or PC.21 clones. The N425K mutation was not found in any of the twenty-two MVC.7 clones but was present in 8 of 13 MVC.14 clones, suggesting this mutation arose between passages 7 and 14 (FIG. 5).

To confirm the frequency of the putative MVC-resistant mutations in the viral populations, an oligonucleotide ligation assay (OLA) was performed using interrogator oligos specific to the mutations R117Q, L/G396V and N425K on gp120 PCR products from cDNA of PC.21 and MVC.21 virus (Table 2). Using this quantitative OLA, we found that the Q117 and V396 sequences were detected at 0.94 and 0.97 frequency in MCV.21 but at 0.55 and 0.32 frequency in the PC.21 virus population, respectively (Table 2). Based on the very low frequency of K425 in the PC.1 and PC.21 populations (~7%) (near the limit of detection at 1%), it appears that the N425K mutation either arose as a de novo mutation in the MVC.21 population or was selected for from a very small fraction of the input virus.

TABLE 2

| Viral | Amino Acid Frequency | | | | | | |
|---|---|---|---|---|---|---|---|
| | 117 | | 396 | | | 425 | |
| Population | R | Q | L | G | V | N | K |
| PC.1 | 0.56 | 0.43 | 0.40 | 0.33 | 0.25 | 0.93 | 0.07 |
| PC.21 | 0.45 | 0.55 | 0.41 | 0.27 | 0.32 | 0.93 | 0.07 |
| MVC.21 | 0.06 | 0.94 | 0.02 | 0.01 | 0.97 | 0.08 | 0.92 |

Sensitivity of Selected A74 HIV-1 Clones to MVC Inhibition

Figure 6:
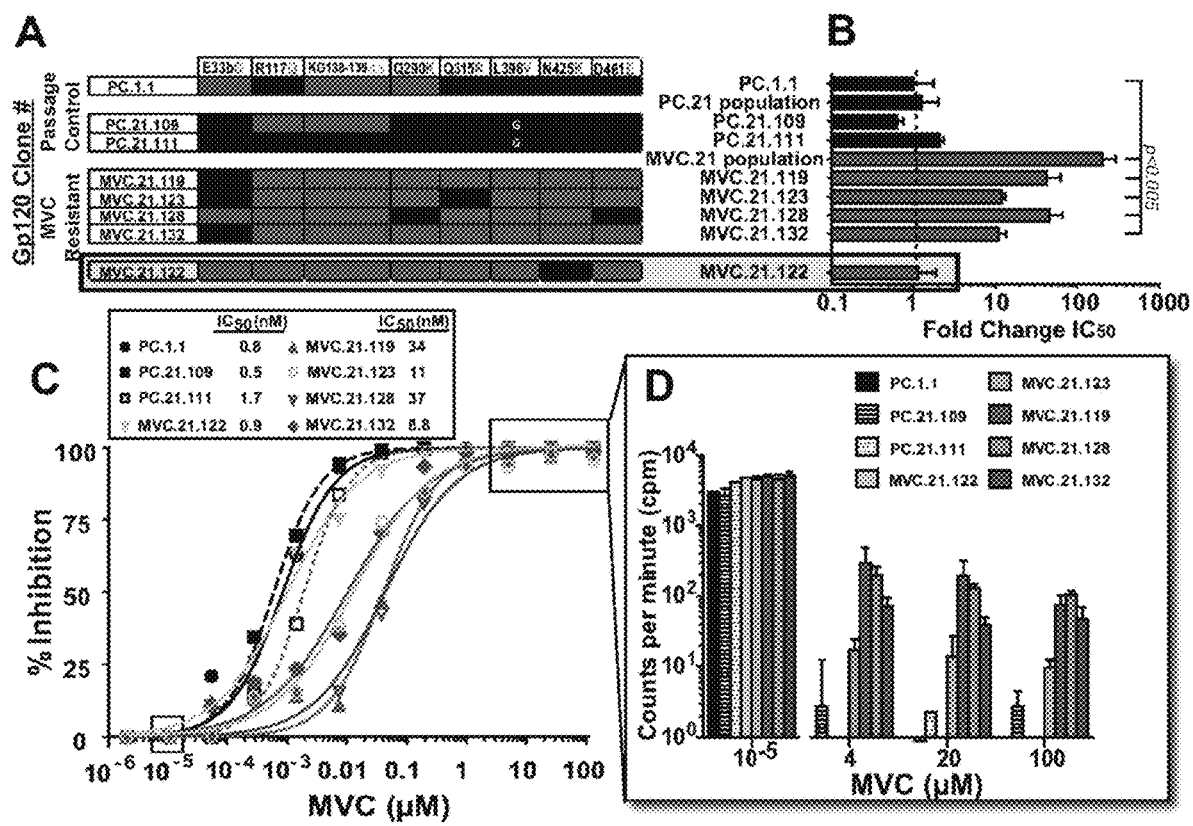
FIG. 6 (A-D) illustrates graphs and a plot showing the sensitivity of gp120 chimeric virus to maraviroc inhibition. (A) Individual gp120 clones from PC.21 and MVC.21 were selected based on differential mutation patterns for MVC drug susceptibility testing in U87.CD4.CCR5 cells. $IC_{50}$ fold change relative to input gp120 clone PC.1.1 are shown in (B). Data represents mean of triplicate wells with standard deviations. (C) Drug sensitivity curves for chimeric gp120 viruses were performed in U87.CD4.CCR5 cells in triplicate. The $IC_{50}$ values are shown to the right of panel (C) whereas the fold change derived from these $IC_{50}$ values are shown in (B) Inhibition curves were generated using Graph- Pad Prism software version 5. (D) Reverse transcriptase activity measured as counts per minute (cpm) for MVC concentrations $1\times10^{-5}$, 4, 20, and 100 µM from which the curves in panel (C) were derived are shown. Data represents triplicates with standard deviations shown.

Based on our cloning strategy, we have a diverse array of gp120 clones with different mutational patterns that represent nearly all combinations of single and multiple substitutions associated with MVC resistance (namely, R117Q, Q290K, L/G396V, D461E, E33bG, N425K and the deletion of K138/G139). This limits the need for site-directed mutagenesis on virus to assess the contribution of each mutation (alone or in combination) to relative MVC resistance. Seven gp120 clones were selected to produce virus from 293T transfections (FIG. 6A), which were then tested for MVC sensitivity in U87.CD4.CCR5 cells (FIG. 6B-D). Although MVC.21.119 and MVC.21.132 share the same mutation profile for the nine MVC-associated amino acid sites in gp120, they do vary slightly in residues at other gp120 sites and are therefore not identical clones. The N33c, K187, G335, E337, K344, E351, I377 and A462 mutations found in MVC.21.119 and not in MVC.21.132 were also identified at high frequency in the passage control.

Clones from the input virus (PC.1.1) and week 21 passage control (PC.21.109 and PC.21.111) were sensitive to MVC inhibition with similar $IC_{50}$ values (FIG. 6B, C). However, clonal viruses derived from MVC.21 varied greatly in $IC_{50}$ values. MVC.21.132 had a moderate 10-fold shift in $IC_{50}$ value to 8.8 nM while MVC.21.119 and MVC.21.128 had pronounced 40-fold shifts in $IC_{50}$ to 34 and 37 nM, respectively (FIG. 6B, C). Importantly, MVC.21.123 retained the wild type V3 mutation Q315 yet still demonstrated a moderate 11-fold $IC_{50}$ shift and was able to replicate at high concentrations (FIG. 6D), suggesting Q315R mutation is not associated with resistance in MVC.21. All four of these clones (119, 123, 128, and 132) had the triad of R117Q, L396V and N425K linked mutations. Clone MVC.21.122 had an $IC_{50}$ value of 0.9 nM similar to that observed for the PC.21 clones despite having the R117Q and L396V mutations.

Despite an apparent "lack" of MPI effect based on the drug susceptibility curves presented in FIG. 6C, viral replication was detected on radiograms. The counts per minute (cpm) were quantified by beta counter (Materials and Methods) for clones 119, 123, 128, and 132 at the highest concentrations of MVC (4, 20, 100 μM) and at $1\times10^{-5}$ μm MVC, which did not result in significant MVC inhibition (FIG. 6C). At the highest MVC concentrations, the level of RT activity for the MVC sensitive clone, PC.21.109 was just above background (<10 cpm) representing 99.9% inhibition (FIG. 6C, D). With the MVC.21.119 MVC resistant clones at these MVC concentrations, the level of RT was 100-300 cpm or >100-fold above background representing 97% inhibition. These differences for the MVC resistant clones were highly significant (p<0.001) and represented a low but consistent MPI effect.

Relative Fitness of MVC-Resistant and Sensitive HIV-1 Clones

The R117Q, Q290K, L/G396V, and D461E mutations have a higher frequency (5-30%) in the HIV-1 subtype A population in the human epidemic whereas the lysine at 425 was found in less than 2% of HIV-1 Subtype A envelope sequences (Table 3) (Los Alamos HIV Sequence Database: www.hiv.lanl.gov). The prevalence of N425K was even lower in other HIV-1 subtypes (B, C, and D) with an occurrence of <0.2% (Table 3). These findings suggest that R117Q, Q290K, L/G396V, D461E, and E33bG have a lower genetic barrier for mutation and less impact on replicative fitness than the N425K mutation. However, we have previously shown that env mutations conferring resistance to entry inhibitors may not always confer a replicative fitness cost. Their low frequency in the HIV-1 population (i.e. low population fitness) may be attributable to other factors such as cellular tropism and sensitivity to neutralizing antibodies or cell-mediated cytotoxic T cell killing. We performed pairwise competitions between three MVC sensitive clones (PC.1.1, PC.21.109, and MVC.21.122) and three MVC resistant clones (MVC.21.119, MVC.21.128, and MVC.21.132) in U87.CD4.CCR5 cells (FIG. 7). It is important to note that even though MVC.21.122 was isolated from the MVC selection, this clone remained MVC sensitive (FIG. 6B-D). Interestingly, all of the MVC resistant clones were actually more fit than MVC sensitive clones PC.1.1 and PC.21.109. The clone (MVC.21.132) with the lowest level of MVC resistance (10-fold) was also the least fit of the MVC resistant clones losing the competition against PC.21.109. In contrast, the MVC sensitive clone, MVC.21.122 (lacking N425K) could compete against the MVC resistant clones suggesting that the mutations (R117Q, Q290K, L/G396V, D461E, and E33bG) may actually confer fitness increases and compensate for the loss of fitness conferred by N425K.

TABLE 3

| | Amino Acid Frequency (%) | | | | | | | | | | |
|---|---|---|---|---|---|---|---|---|---|---|---|
| Total number of | 117 | | | 396 | | | 425 | | | | |
| sequences | R | Q | K | L | G | V | H | K | N | R | Other |
| Group M 61,096 | 0.2 | 1.7 | 97.1 | 0.01 | 0.5 | 99.2 | 0.3 | 0.1 | 97.1 | 2.0 | 0.5 |
| Subtype A 1,065 | 0.2 | 6.3 | 86.7 | 0.1 | 0.1 | 99.8 | 7.8 | 2.0 | 77.0 | 12.3 | 0.9 |
| Subtype B 42,585 | 0.26 | 1.0 | 98.1 | 0.1 | 4.0 | 86.1 | 0.2 | 0.01 | 99.1 | 0.3 | 0.3 |
| Subtype C 11,451 | 0.3 | 0.45 | 97.6 | 0.0 | 1.0 | 77.5 | 0.1 | 0.1 | 98.5 | 0.9 | 0.4 |
| Subtype D 1,450 | 0.2 | 5.8 | 91.8 | 0.0 | 0.1 | 99.9 | 0.6 | 0.2 | 98.3 | 0.2 | 0.6 |

K425 is Primary Resistance Mutation

MVC.21.122 was the only clone from the MVC resistant population that lacked the N425K mutation in the C4 region of gp120 and the only clone not to exhibit an MVC resistance phenotype (FIG. 6B, C). This observation indicated that the K425 mutation was likely essential for resistance in MVC.21. Site directed mutagenesis was performed to introduce the K425 mutation into the MVC.21.122 clone and to confirm the role of this mutation on MVC resistance. Using the same drug inhibition assays described above, we observed a dramatic decrease in susceptibility of MVC.21.122.425K to maraviroc, i.e. a 36-fold shift in $IC_{50}$ from 0.9 nM to 33 nM (FIG. 8A) as well as replication of MVC.21.122.K425 at 100 μM MVC (FIG. 8B).

Shift in IC50 Versus the MPI Effect Denotes MVC Resistance

As described earlier, resistance to CCR5 antagonist is generally related to continued virus replication at even the highest achievable drug concentrations in culture. For example, the CC1/85 MVC-resistant virus containing the T316 and V323 V3 loop mutations is capable of replicating at 25% level in the presence of 1 μM MVC as compared to the absence of drug, however no shift in $IC_{50}$ is apparent. When changes in $IC_{50}$ values have been associated with CCR5 resistance, they have been in the context of reduced maximal inhibition which can be modulated by cell receptor density. With our MVC resistant virus, there is a mixed resistant phenotype. By simply plotting the percent relative inhibition versus drug concentration, the shift in $IC_{50}$ is quite clear and similar to the increases in $IC_{50}$ value characteristic of resistance to all other antiretroviral drugs aside from CCR5 antagonists. In addition to this drug resistance phenotype, the MVC-resistant clones bearing the K425 mutation showed low but significant levels of virus replication at even the highest drug concentrations (FIG. 6D). However, this MPI effect was much less pronounced than with other MVC-resistant viruses as previously reported. Despite MPI values >95% for MVC.21 clones 119, 123, 128, and 132, virus replication was detectable even with 100 μM MVC whereas no replication was observed with the MVC sensitive clones 1, 109, and 122 (FIG. 6D).

Model of K425 in gp120 Structure Suggests Role in CD4 Binding Affinity

Figure 9:
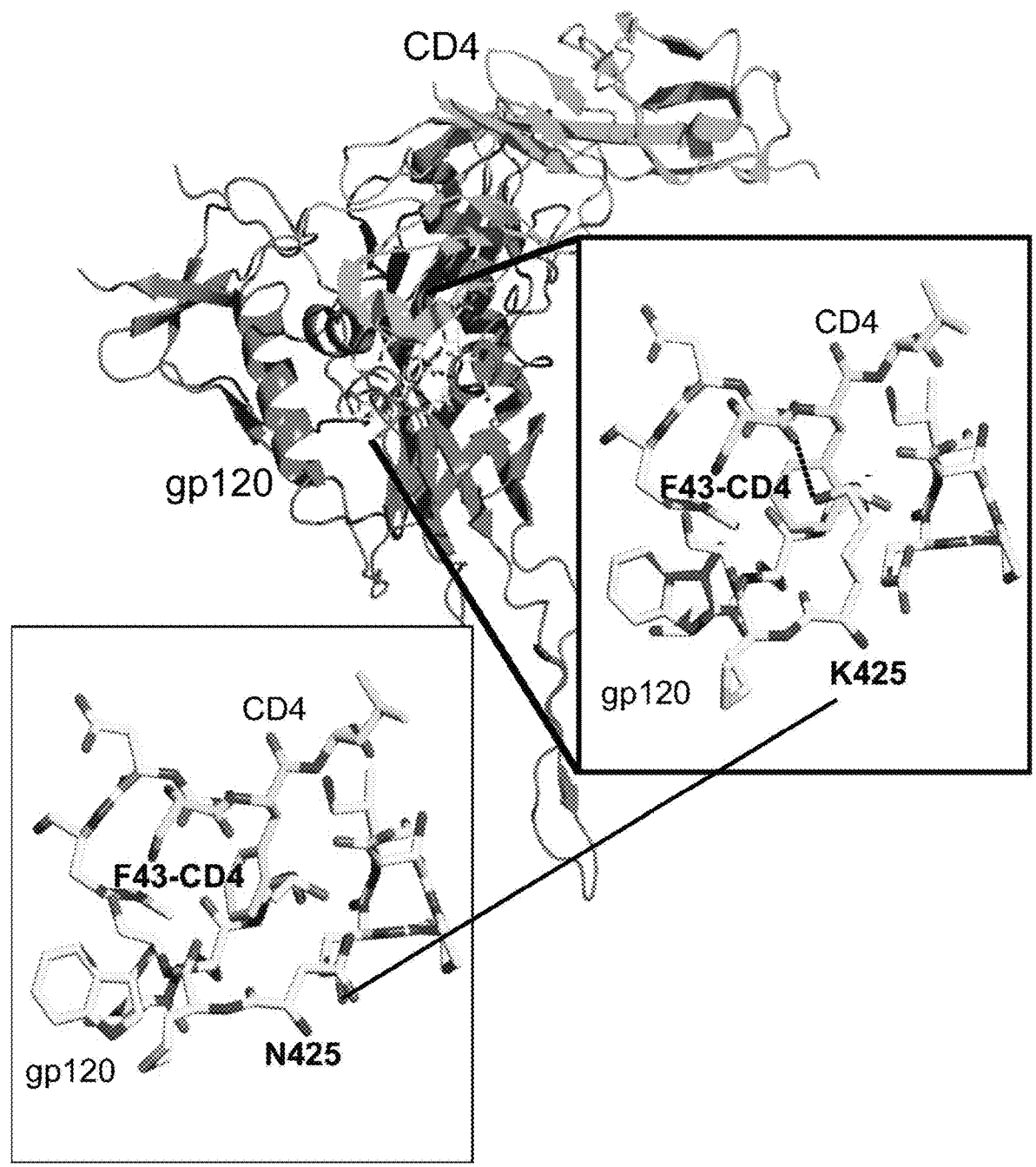
FIG. 9 illustrates modeling of K425 in gp120 HIV-1$_{YU-2}$ virus structure suggests role in CD4 binding affinity. The structure of gp120 HIV-1$_{YU-2}$ complexed with CD4 and 412 Ab (not shown) was used to model the N425 to K mutation. N425 residue lines a cavity in gp120 into which F43 of CD4 projects (inset). Mutation of N425 to K is predicted to form new interactions with F43. (PDB 2QAD)

The N425 residue is located in the β20 sheet of the gp120 bridging sheet as illustrated in FIG. 9 using the crystal structure of HIV-1 gp120$_{YU-2}$ complexed with CD4 and a tyrosine-sulfated 412d antibody. These four anti-parallel beta sheets of gp120 comprise the complete CD4 and partial coreceptor binding sites. This 425 position as either an asparagine or lysine is found distal from the gp120 region thought to interact with the N-terminus of CCR5. However, N425 is specifically located within a cavity known to interact with phenylalanine 43, found within the D1 domain of CD4. N425-gp120 and F43-CD4 are not predicted to form direct interactions. However, when K425 is modeled into the structure using the COOT modeling program, the side chain of K425 is predicted to form a hydrogen bond with the oxygen of S42-CD4 as well as generate a new cation-π interaction between the aromatic ring of F43-CD4 and the Nε side chain of K425.

Example 2

Enhanced CD4 Binding Affinity Novel Mechanism of HIV-1 Resistance to Maraviroc

We previously described in Example 1 an in vitro-derived HIV-1 subtype A MVC resistant isolate which harbored a N425K primary resistance mutation in the C4 region of gp120 but lacked any V3 loop mutations associated with resistance. The location of residue 425 in the crystal structure of gp120$_{YU-2}$ complexed with CD4 suggested a role for enhanced CD4 binding in the mechanism of MVC resistance of this virus. In this Example, we compared resistance profiles of this subtype A virus (A74.MVC.21) with a subtype B patient-derived MVC resistant virus (R3) previously shown to utilize drug-bound CCR5. Unlike the subtype B resistant virus, the in vitro-derived resistant virus did not exhibit a resistance profile in single cycle assays but rather demonstrated an increase in half-maximal inhibitory concentration ($IC_{50}$) under multiple replication cycle conditions. This virus was capable of binding soluble CD4 with high affinity, displayed efficient use of low level CD4 in 293 Affinofile cells, exhibited faster fusion kinetics and higher replicative fitness. Our findings show that MVC resistance is mediated by enhanced CD4 binding affinity through a competitive resistance mechanism.

Materials and Methods

Cells, Viruses and Inhibitors

U87.CD4.CCR5 and 293T cells were maintained as previously described. 293 Affinofile cells are a HEK293 derived cell line dually inducible for CD4 and CCR5 expression. This cell line was generated by the sequential transduction of transactivators and the inducible promoters for expressing CD4 and CCR5. CD4 and CCR5 receptor expression can be simultaneously and independently induced with doxycycline and ponasterone A (ponA), respectively. 293 Affinofile cells were maintained in DMEM supplemented with 10% dialyzed FBS, 100 μg/mL penicillin/streptomycin, and 50 μg/ml blasticidin. Prior to use, surface receptor expression of CD4 and CCR5 were determined by quantitative fluorescence-activated cytometry (qFACS) analysis using either phycoerythrin-conjugated mouse anti-human CD4 antibody (clone Q4120; Invitrogen, Carlsbad, Calif.) or phycoerythrin-conjugated mouse anti-human CCR5 antibody (clone 2D7; BD Biosciences, San Jose, Calif.). Duplicate 6-well plates were seeded with $2\times10^5$ cells/well and CD4 and CCR5 expression were induced the following day using doxycycline and Ponasterone A, respectively. Cells were induced using 2-fold dilutions from 0-2 ng/mL of doxycycline (CD4) and 0-2 μM of PonA (CCR5) for 24 hours. Surface receptor expression levels were quantified. 293 CD4 cells, are a HEK293 cell line stably transduced with the MV7neo-T4 retroviral vector encoding human CD4. These cells were maintained in complete media supplemented with 300 μg/mL G418.

Gp120 chimeric replication competent viruses were generated. Psuedoviral particles were generated by cotransfection of 293T cells with pREC_NFL_gp120 plasmids and pNL.Luc.AM psuedotyping vector. Expression vectors encoding envelopes of viruses S2 and R3 were provided. Gp120 regions of S2 and R3 were PCR amplified and cloned by yeast homologous recombination into pREC_NFL_Δgp120/URA3 as previously described. Sequencing confirmed the integrity of the cloned regions regarding MVC resistance mutations.

Maraviroc and TAK-779 were diluted in PBS and filter sterilized. C34 and recombinant human soluble CD4 (2 domain) produced and purified from Escherichia coli were obtained through the AIDS Research and Reference Reagent Program, Division of AIDS, NIAID, NIH. Recombinant human soluble CD4 (4 domain) produced using recombinant baculovirus vectors and secreted from insect cells was purchased from Protein Sciences Corporation, Meriden, Conn.

Structural Modeling

The location of MVC resistance mutations were identified using the crystal structure of gp120 HIV-1$_{YU-2}$ with CD4 and tyrosine-sulfated antibody 412d (PDB ID: 2QAD). Sequence alignment of gp120$_{YU-2}$ with A74.PC.21 indicated relative homology in the C4 region. Using 2QAD as a template, the K425 mutation was modeled into the structure using the COOT structural modeling program. The local structure was regularized with slight torsion of the lysine side chain resulting in two potential new interactions: a hydrogen bond with S42 and cation-π interaction with aromatic ring of F43 of CD4. This structural model was also compared to a high resolution structure of gp120 in complex with CD4 and a CD4i antibody 17b (PDB ID: 1G9M). The Nε of K425 in the structural model superimposed well with a bound water molecule in the binding pocket of F43 from the 1G9M crystal structure.

Drug Susceptibility Assays

For single replication cycle drug susceptibility assays, U87.CD4.CCR5 cells in 96-well format ($1 \times 10^4$ cells/well) were pretreated for 2 hours with 10-fold dilutions of MVC (1 µM to $1 \times 10^{-7}$ µM) then infected in triplicate with luciferase encoding psuedovirus. After 48 hours, supernatant was removed and cells were lysed using 50 µL Glo lysis buffer (Promega, Madison, Wis.). Cells were lysed for 20 minutes at room temperature, transferred to white polystyrene 96 well plates, and read with a PerkinElmer VICTOR plate reader using injectors to introduce 50 µL Bright Glo reagent per well (Promega, Madison, Wis.). Luciferase activity was measured as relative light units (RLU).

For multiple replication cycle drug susceptibility assays, U87.CD4.CCR5 cells were plated as above and pretreated with 5-fold dilutions of MVC (100 µM to $2 \times 10^{-6}$ µM). Cells were infected at an MOI of 0.001 IU/cell with NL4-3/gp120 chimeric virus in quadruplicate. After 24 hours, viral inoculums were removed and replaced with media containing the appropriate MVC dilutions. Reverse transcriptase activity in supernatant was monitored as previously described on days 4 through 7 post infection.

sCD4 Activation and Inhibition Assays 293T or 293.CD4 cells ($1 \times 10^6$ cells) were plated in 10 $cm^2$ tissue culture dishes and transfected with 6 µg pBABE.CCR5 plasmid (AIDS Research and Reference Reagent Program, Division of AIDS, NIAID, NIH) using Fugene 6 tranfection reagent (Invitrogen). After 24 hours, cells were plated in 96-well plate format at a density of $1 \times 10^5$ cells/well. Normalized amounts of psuedoviruses were preincubated with 20 or 200 nM of 4 domain sCD4 (Protein Sciences Corporation, Meriden, Conn.) at 37° C. for 30 minutes prior to infection. Cells were infected in triplicate and luciferase activity measured 48 hours after infection as described above. Fold change in RLU as well as percent inhibition were measured relative to the luciferase activity of the no sCD4 condition.

For sCD4 titration assays, 293T or 293.CD4 cells were treated in the same manner described above. Cells were plated in 96-well plate format at $1 \times 10^5$ cells/well after CCR5 transfection. Cells were treated with 4-fold dilutions of 2 domain sCD4 (25 µg/mL to 0.001 µg/mL) and then infected with psuedoviruses in triplicate. Luciferase activity was measured 48 hours after infection.

CD4/CCR5 Receptor Affinity Assays

293 Affinofile cells were plated in 96-well format ($1.5 \times 10^4$ cells/well) and CD4 and CCR5 receptor expression was induced the following day. Maximal and minimal receptor expression was induced for each receptor in triplicate columns of the plate using 2 ng/mL and 0.03 ng/mL doxycycline for CD4 and 2 µM and 0.03 µM Ponasterone A for CCR5. In rows, the alternate receptor expression was induced in 2-fold serial dilutions (8 dilutions) from 0-2 ng/mL doxycycline (CD4) and 0-2 µM PonA (CCR5). This induction scheme results in 32 distinct CD4 and CCR5 surface expression profiles. Cells were incubated at 37° C. for 24 hr prior to infection. Cells were infected in triplicate with normalized psuedovirus and luciferase activity measured 48 hours after infection as described above. Maximal infection was considered to be the luciferase activity measured for the highest induction of both CD4 and CCR5 and percent infection was calculated relative to this condition.

Kinetic Fusion Assay

U87.CD4.CCR5 cells ($5 \times 10^5$ cells) were spinoculated with psuedovirus at 2500×g at 4° C. for 90 minutes. Cells were then plated in 96-well plates at $1 \times 10^5$ cells/well in 50 µL 4° C. cold media. Infection was synchronized by addition of 130 µL/well media prewarmed to 37° C. This was considered time 0 post-infection. At time intervals post infection, 20 µL of the fusion inhibitor C34 (100 µM final) was added to triplicate wells. Cells were incubated at 37° C. for 48 hours and luciferase activity was measured. Relative infection was calculated based on the maximal luciferase activity observed for each virus at three hours post-infection.

Results

Differential Maraviroc Resistance Profiles

Multiple studies of CCR5 antagonist resistant viruses have described an inability to completely suppress viral replication at high drug concentrations. This has been attributed to mutations in the gp120 glycoprotein, particularly the V3 loop, that permit interactions with drug bound conformations of CCR5. However, we have shown that while MVC resistant virus A74.MVC.21 continues to replicate at high drug levels, the primary resistance mutation is located in a region of gp120 which comprises the CD4 binding site and is unlikely related to altered CCR5 binding. To better understand the resistance of A74.MVC.21, we compared this virus with another MVC resistant isolate (R3) which was derived from a patient failing MVC therapy in the SCOPE cohort and was shown to utilize MVC-bound CCR5 for entry.

As shown in FIG. 10, maraviroc resistant viruses A74.MVC.21 and R3 differ in primary resistance mutations. The primary resistance mutation for virus A74.MVC.21 was previously mapped to a K425 mutation in the C4 region of gp120 with mutations Q117 and V396 in other regions of gp120 appearing associated with resistance in this isolate. Alternately, the primary resistance mutation identified in the R3 virus was a H308 mutation in the V3 loop region with V3 mutations H320 and V322a as well as a V4 loop mutation G407 modulating the level of resistance. When comparing the location of these resistance mutations in a structure of HIV-1 gp120$_{YU-2}$ in complex with CD4 and antibody 412d (PDB: 2QAD) we noticed that residue 425 was located proximal to the F43 residue of CD4 (FIG. 10), a residue known to be critical in gp120-CD4 binding interactions. Modeling of the N425K transition (inset) revealed new potential interactions between side chain of K425 and F43, specifically a cation-π interaction with the aromatic ring of the phenylalanine. Additionally a new hydrogen bond could be formed with S42 of CD4. This structural model was also compared to a high resolution structure of gp120$_{HXBc2}$ in complex with CD4 and a CD4i antibody 17b (PDB ID: 1G9M). The Nε of K425 in the structural model superimposed well with a bound water molecule in the binding pocket of F43 from the 1G9M crystal structure. This model suggests a role for CD4 binding in A74.MVC.21 resistance to maraviroc. In contrast, the H308 primary resistance mutation of virus R3 is located in the stem of the V3 loop, a region believed to interact with the second extracellular loop of the CCR5 coreceptor. R3 has previously been shown to utilize inhibitor bound CCR5 for entry and was sensitive to alanine substitutions in both the N terminus and extracellular loops of mutant CCR5 receptors.

In addition to genotypic differences, the phenotypic resistance profile of NL4-3/gp120 chimeric viral clones derived from A74.MVC.21 differed from those described for other MVC resistant viruses in that resistance was observed as increases in the concentration of MVC required to suppress viral replication by 50% ($IC_{50}$). To directly compare resistance profiles of A74.MVC.21 derived gp120 clones and clone R3 in a similar genomic background, the gp120 regions of R3 and the pretreatment sensitive clone S2 were PCR amplified and cloned by yeast homologous recombination into pREC_NFL_Δgp120/URA3. Replication competent viruses as well as luciferase expressing psuedoviruses were generated for A74.PC.21.109, A74.MVC.21.132, S2, and R3 as described. Both single cycle and multiple replication cycle drug sensitivity assays were performed in U87.CD4.CCR5 cells (FIG. 11). Strikingly, resistance could not be detected for A74.MVC.21.132 in single cycle assays (FIG. 11A) but was clearly indicated by a 17-fold rightward shift in $IC_{50}$ value as compared with the MVC sensitive clone A74.PC.21.109 in multiple replication cycle conditions (FIG. 11B). In direct contrast, resistance for clone R3 was observed as a reduction in the maximal percent inhibition (MPI) to 56% and 61% under both single and multiple cycle conditions, respectively (FIG. 11C, D). The differential resistance profiles obtained for A74.MVC.21.132 and R3 in addition to the location of the resistance mutations in the gp120 structure suggested a mechanism of resistance for A74.MVC.21.132 unrelated to utilization of inhibitor bound CCR5.

Recombinant Human Soluble CD4 Enhances Infection of A74.MVC.21.132

Given the proximity of the K425 mutation of A74.MVC.21 to the putative binding site of CD4, we wanted to determine whether soluble CD4 (sCD4) could mediate entry of A74.MVC.21.132 into cells that did not express cell surface CD4. At non-inhibitory concentrations sCD4 can act as a surrogate for cell bound CD4, inducing the conformational changes in gp120 required for coreceptor binding and permitting infection of CD4 negative cells. This enhancement of virus infection or activation by sCD4 has been described for some SIV, HIV-2 and HIV-1 strains and seems to correlate with high CD4 binding affinity. The concentration of sCD4 required to induce enhancement of infection can vary widely dependent on viral strain.

In the absence of sCD4, neither the sensitive or MVC resistant viruses were able to infect cells lacking surface CD4. However, resistant virus A74.MVC.21.132 was able to infect CD4 negative cells in the presence of 20 nM and 200 nM sCD4 demonstrating 3-fold and 2-fold increases in RLU, respectively (FIG. 12A). Sensitive viruses A74.PC.21.109 and S2 were not able to infect cells even in the presence of sCD4 while resistant virus R3 displayed a 1.4-fold increase in RLU at 200 nM sCD4. To determine whether sCD4 could enhance infection in cells that expressed surface CD4, 293 cells stably expressing CD4 were transfected with CCR5 and infected with psuedovirus pretreated with sCD4 in the same manner as CD4 negative cells (FIG. 12B). While all viruses were able to infect these CD4+CCR5+ cells, again the A74.MVC.21.132 virus demonstrated an enhancement of infection with 5.2-fold higher RLU activity at 20 nM sCD4 and 2.7-fold higher activity at 200 nM as compared to psuedovirus that was not preincubated with sCD4 prior to infection. In contrast, infection of A74.PC.21.109 was inhibited by 11 and 32% at these concentrations, respectively. Infectivity of virus S2 was relatively unaffected by these concentrations of sCD4 while the resistant virus R3 showed only a 1.6-fold change in RLU at the highest sCD4 concentration tested (FIG. 12B).

The enhancement of infection of A74.MVC.21.132 by sCD4 in both CD4 negative and CD4 positive cells suggested this virus was binding sCD4 with higher affinity than the A74.PC.21.109 virus. However, the reduction in fold change RLU of A74.MVC.21.132 at 200 nM versus 20 nM sCD4 indicated this effect was concentration dependent and that at higher concentrations this virus may be inhibited by sCD4. To further examine sCD4 effects on A74.MVC.21.132 and determine requirements of CD4 domains, a titration curve using the recombinant D1-D2 form of sCD4 produced in bacteria was performed in 293T and 293.CD4 cells transfected to express CCR5 (FIG. 13). Recapitulating the results using sCD4 (D1-D4), the 2 domain peptide permitted infection of CD4 negative cells for virus A74.MVC.21.132. A steady enhancement of infection was observed for A74.MVC.21.132 up to 0.4 μg/mL sCD4. Beyond this concentration, RLU activity decreased to a level observed at the lowest drug concentration (FIG. 13A). Interestingly, in 293.CD4 cells expressing CCR5 infection also appeared enhanced up to 0.4 μg/mL at which point the level of infection declined rapidly for A74.MVC.21.132 resulting in complete suppression of virus infection by 6.25 μg/mL (FIG. 13B). The resultant $IC_{50}$ for A74.MVC.21.132 was 1.5 μg/mL. Alternatively, A74.PC.21.109 appeared less sensitive to inhibition by sCD4 with viral infection suppressed by only 50% at the highest concentration tested (25 μg/mL). Together the data in FIGS. 12 and 13 suggested that in a concentration dependent manner sCD4 could induce the necessary conformational changes in gp120 of the MVC resistant virus A74.MVC.21.132 to permit entry into CD4 negative cells. Beyond a threshold concentration however, A74.MVC.21.132 became sensitive to inhibition of CD4 positive cells potentially through a competitive binding mechanism between sCD4 and cellular CD4 for gp120 binding.

Efficient Infection of Cells with Low Levels of Surface CD4

We next measured the ability of A74.MVC.21.132 to infect cells that express low levels of surface CD4 (FIG. 14). 293 Affinofile cells have dual inducible markers for variable and independent expression of both CD4 and CCR5. Based on quantitative flow cytometry we determined the concentrations of doxycycline and ponasterone A required to induce minimal CD4 and CCR5 expression, respectively. In FIG. 14, the results of low CD4 and low CCR5 induction across a range of alternate receptor expression levels are depicted. The low CD4 induction condition resulted in approximately 3000 receptors per cell. The A74.MVC.21.132 virus was particularly adept at utilizing low levels of CD4 to mediate infection of cells across a wide range of CCR5 receptor surface expression compared to A74.PC.21.109 which lacked the K425 mutation (FIG. 14A). Similarly, under low CCR5 surface expression levels (5000 receptors per cell), A74.MVC.21.132 was more efficient at infecting cells at the lower CD4 expression levels than A74.PC.21.109 (FIG. 14B).

Maraviroc Resistant Virus Demonstrates Increased Sensitivity to CD4 Mimetic

If K425 binds with greater affinity to F43 of CD4 then it is possible that this resistant virus may also bind CD4 derived compounds designed to mimic the binding of F43 to gp120 with greater affinity. Enhanced binding to a CD4 mimic would deprive the virus of the ability to bind cell surface CD4 and inhibit entry. To test this hypothesis, drug susceptibility assays were performed in U87.CD4.CCR5 cells in the presence of decreasing concentrations of the attachment inhibitor BMS-806. BMS-806 is a first generation attachment inhibitor specifically designed to mimic F43-CD4 and bind to gp120 within the F43 binding pocket. FIG. 15 shows that at the highest concentrations tested (50 and 5 µM), MVC.21 is inhibited to a greater extent (98%) than is the maraviroc sensitive PC.21 virus (46%). Although inhibition by this compound is weak for the parental virus, this data would suggest an increase in sensitivity to the attachment inhibitor for MVC.21, likely as a result of tighter binding of the compound within the F43 binding pocket. Since K425 is the only amino acid different between MVC.21 and PC.21 within this binding pocket, it is reasonable to surmise that K425 enhanced binding affinity to BMS-806 and was thereby more easily blocked from binding surface CD4.

Maraviroc Resistant Virus Exhibits Faster Entry Kinetics

Figure 16:
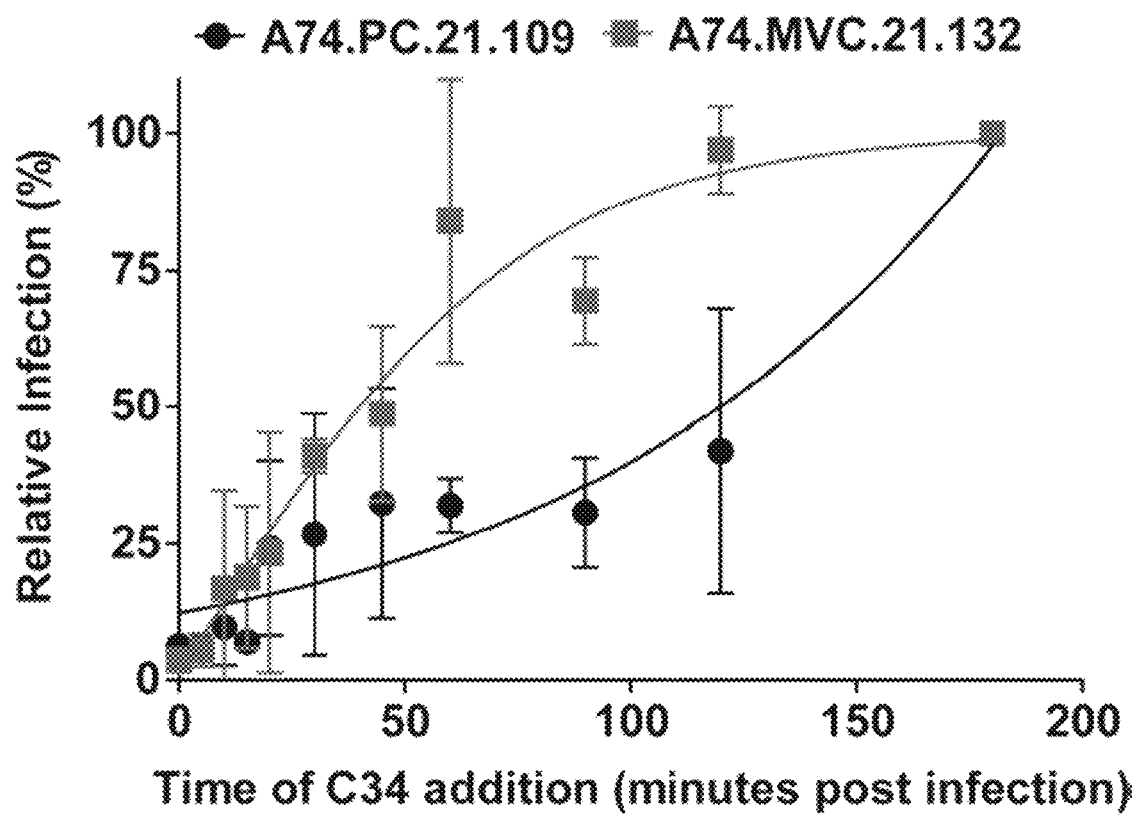
FIG. 16 illustrates a plot showing that maraviroc resistant virus demonstrates enhanced fusion kinetics. Time of drug addition assays were performed in U87.CD4.CCR5 cells using luciferase encoding psuedovirus particles to score fusion. An $IC_{99}$ concentration of the fusion inhibitor C34 was added to cells at the indicated time intervals post infection. Relative infection was measured based on the maximal fusion scored for each virus at 3 hours post infection. Data represents triplicates with standard deviations shown. Curves were generated using nonlinear regression curve fitting features of GraphPad Prism 5 software.

Mutations affecting either CD4 or CCR5 binding have been shown to influence viral entry kinetics, including mutations associated with CCR5 antagonist resistance. To assess the impact of the resistance mutation K425 on viral fusion kinetics we performed a time of drug addition assay using the fusion peptide C34 in U87.CD4.CCR5 cells (FIG. 16). The sensitive A74.PC.21.109 virus exhibited a half-maximal time of fusion ($t_{1/2}$) of 120 minutes. In comparison, the rate of fusion for the A74.MVC.21.132 resistant virus was three times faster with a $t_{1/2}$ of only 40 minutes. This would suggest that not only does K425 significantly impact the interactions of this virus with CD4, but also enhances the overall rate of the entry process.

Example 3

We have identified an MVC-resistant virus conferred by an N425K gp120 mutation. Surprisingly, K425 is found at very low frequencies in the HIV-1 population despite having a selective advantage based on its replicative fitness and entry efficiency. Low prevalence of K425 in Env gp120 may relate to its ability to elicit protective CD4i Abs, I.e. an attribute that would limit virus survival. In addition, K425 HIV-1 may have enhanced sensitivity to CD4i Ab inhibition. All of these findings indicate that the N425K gp120 can be an effective core for an HIV-1 vaccine. Of course, the key element of N425K gp120 in a vaccine would relate to the higher binding affinity to CD4, which could hold gp120 in a CD4i transitional state long enough to elicit CD4i Abs. Just the nature of enhanced interaction with CD4+ antigen presenting cells could justify the inclusion of N425K into most vaccine constructs.

We employ a series of innovative technologies and experiments to determine the structure of this unique gp120 and to probe the CD4 induced conformation, taking advantage of a more stable CD4-gp120 complex for X-ray crystallography studies. We utilize our novel yeast-based cloning strategy to produce both our vaccine constructs and recombinant virus for Nab testing. The SHIVenv vaccine construct is produced from a safe, three vector system which is similar to gene therapy vectors. Our unique transgenic mouse expressing human CD4 on B cells (huCD4-B mice) should provide a strong animal model to determine if the N425K Env-based vaccines can elicit CD4i Nabs. Preliminary data shows that the N425K Env vector binds with higher affinity for the CD4+ cells than the wt N425 vector. Although this vector cannot replicate in huCD4+ mouse B cells, the SHIVenv vector was designed (and tested) to enter and express HIV-1 Env in macaque CD4+/CCR5+ cells and is currently being employed in macaque immunizations studies. Thus, we can quickly transition to macaque studies following the N425K Env-based vaccines in the huCD4-B mouse model.

We examine the humoral response to the SHIV vectors expressing the N425K mutations placed in the Env of different subtypes (A, B, C, D, and CRF02_AG). Although the CD4 binding site in the C4 domain of gp120 is relatively well conserved, the CD4i epitopes and surrounding sequences are more variable between subtypes. We construct and produce the HIV-1env counterparts for Nab screens with mouse (or macaque sera). These Abs are tested for inhibition of the parental wt and N425K HIV-1 clones, examined for within and cross-clade neutralization, screened for inhibition of tier I-IV HIV-1, and finally, are purified from hybridomas for further structural analyses with soluble CD4-gp120.

HIV-1 Envelop Glycoproteins with Enhanced CD4 Binding and Sensitivity to CD4i Abs General Procedure The N425K MVC-resistant mutation was selected from a subtype A HIV-1 strain. N425K is introduced into different HIV-1 env's from subtype A, B, C, 0, and CRF02_AG using a yeast-based cloning method. Chimeric virus containing these N425K envs is then be tested for sensitivity to various Nabs and patient sera. CD4 binding affinity of the virus is measured using soluble CD4 and the Affinofile system, i.e., a cell line expressing controlled CD4 and CCR5 under different in ducible promoters. Recombinant subtype B gp120s are produced with or without K425 for crystallization to determine Ab and CD4 binding. These analyses complement X-ray crystallography and structural mass spectrometry approaches to characterize CD4 bound structures of the N425 and K425 gp120 with (or without) new CD4i Abs, i.e., isolated from the vaccinated mice.

Cloning and Production of N425K Virus and Vaccine Vectors

Figure 18:
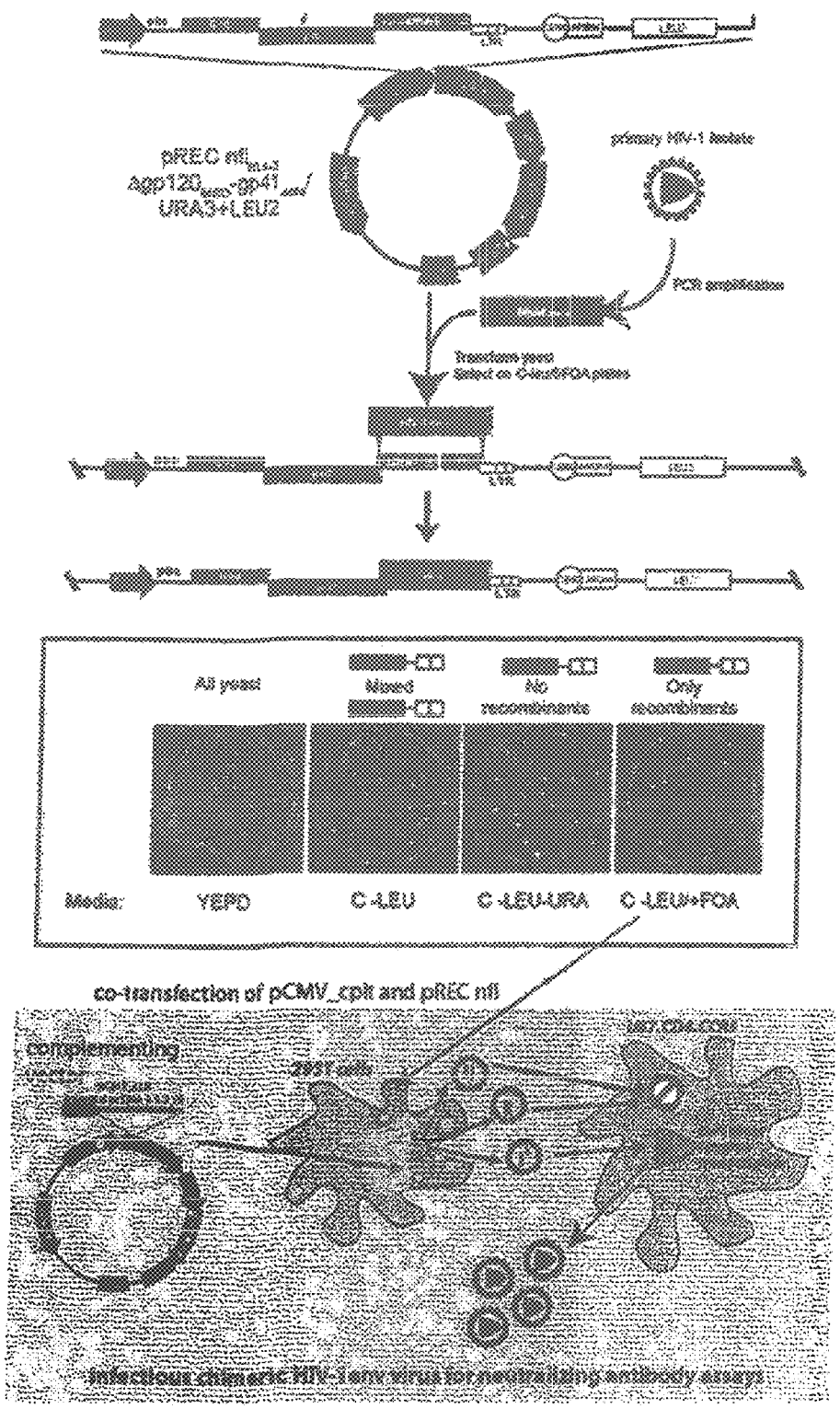
FIG. 18 is a schematic showing env cloning for neutralizing antibody assays.
Figure 19:
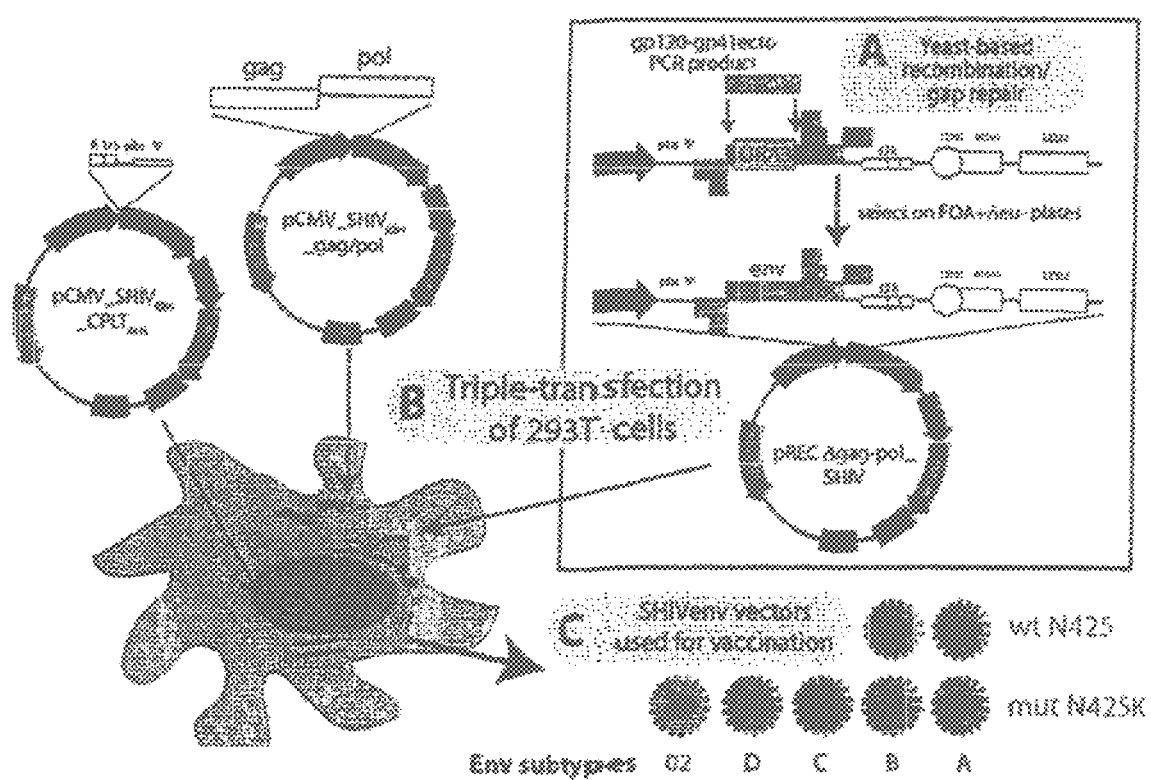
FIG. 19 is a schematic showing vaccine vector production.

We have developed a yeast-based cloning strategy to rapidly introduce any HIV-1 region into various HIV-1 backbones. Over 1000 chimeric or site-directed mutants of HIV-1 have now been produced and employed in several research articles. The system for yeast based cloning followed by production of replication-competent virus or of vaccine vectors is described in FIGS. 18 and 19, respectively. Using PCR mutagenesis, the N425K mutation is introduced into each of five CCR5-using env genes from the subtype A isolate, (A)74-UG, (8)6-91 US714, (C)5-97ZA003, (D)76-UG, and (02_AG)BD6-15, i.e., the virus cladeslrecombinants representing >95% of the infections worldwide. These primary HIV-1 isolates have been extensively analyzed by our laboratory. The HIV-1 env PCR product is co-transfected into yeast with a (1) linearized pREC nfl$_{NL4-3}$Δgp120MSD-gp41 ecto/URA3+LEU2 vector (pub.x). (FIG. 18) and (2) linearized pREC Δgag-pol_SHIVenvΔgp120MSD-gp41 ecto/URA3+LEU2 vector vaccine vector (FIG. 19A). The URA3 gene converts FOA into a toxic anabolite such that the only yeast colonies to survive on FOA+/leu– plates will have recombined in the env PCR product in place of URA3 (FIG. 18). Recent studies indicate that cloning the entire env commonly results in complementation problems related to splitting of the rev/tat coding regions, i.e., first exon from NL4-3 vector and second exon from the primary HIV-1 isolate. However, we have 90% success in obtaining functional chimeric virus with our gp120-gp41 ecto (extracellular domain) construct. Complementation of non-subtype 8 gp120-gp41ecto domains within subtype 8 NL4-3 backbone is surprisingly efficient in terms of producing replication competent virus. Nonetheless, if difficulties arise with the NL4-3 backbone, we introduce the wild type and mutant envs into our pREC nfl derived from the subtype A, C, and CRF02_AG infectious clones.

Chimeric Virus and Vaccine Vector Production

The approach for virus or vaccine production after cloning is straightforward and involves (1) co-tranfection of 293T cells with the pREC nfl construct (containing near full length genome) and our complementing vector (pCMV_ cplt 5'LTR). (FIG. 18) or (2) co-transfection of 293T cells with pRECΔgag-pol_SHIV+pCMV_SH1V_gag/pol+ pCMV_SHIV_cplt (FIG. 19). For procedure (1), we have optimized our system such that the complementing HIV-1 RNA and nfl HIV-1 RNA are packaged with equal efficiency into new virus particles. Only the heterodiploid virus, representing 50% of the virus produced from 293T transfected cells, can complete the reverse transcription cycle and produce fully infectious virus following de novo infection. Using this system, we obtain chimeric HIV-1 in less than one week from start to finish. This virus will be employed in our assays to determine CD4 binding affinity, replicative fitness, sensitivity to Nabs including CD4i Abs, and MVC sensitivity.

For procedure (2), we produce a safe and effective vaccine vector (defective aka dSHIVenv) to immunize mice and for use with macaques. We employ a SHIV system where the Env glycoprotein is derived from vector expressing mRNA as a mini HIV-1 genome (Δgag-pol). Briefly, the SIVmac239 Gag-Poi proteins are expressed from a separate plasmid (pCMV_SHIV_gag/pol; FIG. 19). The mRNA from this plasmid lacks the packaging element to prevent encapsidation but does have the RRE to boost nuclear export by Rev and to support strong Gag-Pol protein expression. The HIV-1 Env glycoproteins originates from a co-transfected plasmid (pREC,1gagpoCSHIV) expressing a defective HIV-1 gRNA that lacks all HIV-1 genes except env, rev, and tat and still harbors the primer binding sequence, the essential RNA packaging elements, and 3'LTR. Just as in procedure (1), the third plasmid (pCMV_SHIV_cplt) expresses the complementing $SIV_{mac239}$ U5-R-pbs-Ψ (packaging) RNA which together with the Δgag-pol SHIV gRNA will produce a defective proviral DNA for integration and subsequent expression of only HIV-1 env. In our transgenic mouse system, the vaccine vector can bind to the human CD4 on mouse B cells but cannot enter or infect due to a lack of CCR5. Nonetheless, this vector is effective at eliciting a humoral response.

Replicative Fitness

We have shown that the N425K subtype A HIV-1 was more fit than the N425 virus clones and expect similar results with N425K in other subtypes. To access the impact of the N425K mutations in other backbones (especially in subtype B), we will need to determine relative replicative fitness as well as CD4 binding affinity, and sensitivity to Nabs. Our fitness assay has been previoulsy described. Briefly, the parental chimeric virus from each subtype (e.g., NL4-3EnvA, EnvB, etc) and the respective N425K mutant viruses (e.g., NL4-3Env$A_{N425K}$, NL4-3Env$B_{N425K}$, etc) will be added at equal MOIs (multiplicities of infection; 0.01) to U87.CD4.CCR5 cells or PHAJ112-treated PBMCs. The relative virus production from these head-to-head competitions will be monitored by a quantitative oligonucleotide ligation assay (OLA). OLA is relative new procedure where a cycling ligase only covalently links oligonucleotide probes that anneal to the target sequence and that abut against a single nucleotide polymorphism of interest. We have recently described this procedure as well as detection/quantitation of ligated products via luminex beads. Basically, we accurately quantify the amount of N425 (wt) versus K425 (mut) virus from viral RNA extracted from cell-free supernatant, converted into cDNA, and then PCR amplified prior to OLA. We have compared this procedure to more laborious cloning+Sanger sequencing as well as next gen sequencing and found quantitative OLA relatively inexpensive, rapid, and highly accurate. These other procedures remain as a backup but quantitative OLA for HIV-1 competitions has been utilized extensively by our group.

Affinofile to Measure Efficiency of Virus Entry and CD4 Usage

We adopt the Affinofile system to measure the efficiency of HIV-1 entry into a new 293T cell line with expression of CD4 and CCR5 under the control of different inducible promoters. Using the Affinofile system, we have shown that the MVC-resistant N425K virus, as compared to the wt K425 virus, was able to utilize lower levels of CD4 per cell for entry. This analyses is repeated with the N425K introduced into the other subtypes. Briefly, CD4 expression (2000 to 100,000/per cell) across the rows of a plate and increasing CCR5 (1000 to 20,000), across the columns are modulated by treatment with minocycline (0.16 to 5 μM) and ponesterone (0.015 to 2 μM), respectively. The same amount of virus (0.01 MOI) is then used to infect 48 well plates. We can monitor HIV-1 infection via a Gaussian luciferase under the control of the HIV-11 TR promoter. Several mathematical models are used to compare the HIV-1 infectivity across the range of CD4 and CCR5 levels on the cell surface and to establish the relative utilization/affinity for each receptor during infection. N425K in all HIV-1 subtype backbones is capable of using low levels of CD4 for entry better than the parental N425 viruses.

Sensitivity to Nabs and Patient Sera

Three basic cell types/systems are used to measure inhibition by monoclonal Nabs and Nabs as part of whole patient sera. These include the use of TZM-BL cells, the Affinofile cells with high CD4/low CCR5, and PHAJ11-2 treated CD4+ T cells. In general, CD4i Abs do not efficiently neutralize virus in the TZM-BL cells due to very high (above physiological) levels of CCR5. CCR5 competes for gp120 binding with CD4i Abs. The most appropriate conditions to test for Nab activity remains PBMCs but unfortunately the level of inhibition may be donor dependent. For these assays, we will pool together CD4+ T cells (isolated by negative selection) from ten different donors. These cells are PHA activated prior to freezing, and thawed then incubated with Il-2 prior to use. Finally, we have started assays for Nabs and sera using the Affinofile cells with high CD4 (−50,000 molecules per cell)/low CCR5 (2500), i.e., conditions similar to primary T cells. Regardless of the cells in the assay, various Nabs classified as specific for CD4i, glycan, and gp41 MPER will be added to cells at 50 μg/ml to 0.5 ng/ml along with the various N425 wt and N425K mutant viruses. Virus production will be measured by luciferase activity with TZM-BI cells, viral RT activity in the supernatant with primary CD4+ T cells, and Gaussian luciferase with the Affinofile cells. The EC50 concentrations are determined for each. Finally, we also have a panel of over 1000 stored sera from subtype A, B, C, D, and CRF02_AG infected patients from Uganda. All samples are subtyped but are de-identified of any other clinical parameters/demographics from viremic patients. Five sera from Subtype-matched and five from different subtype infections will be serially diluted (1/4 dilutions) and added to various cell types with the N425 wt and N425K mutant viruses. The N425K mutant viruses will be more sensitive to CD4i Abs but both N425 and K425 viruses may have comparable sensitivity to neutralization from sera of both subtype matched and different patients.

Effects of Soluble CD4 and Sensitivity to MVC

Binding Affinity of Virus to Cells

We utilized a method to compare binding affinity of two viruses for a susceptible cell. Briefly, 0.1 Mal of N425 wt virus is incubated at 1SoC for 1 hr on suspension CD4+CEM cells with or without CCRS. This lower temperature prevents virus-cell membrane fusion. The cell-virus mixture is then aliquoted and the competitor K425 virus is added at a different concentrations (increasing from 0.0001 MO1 to 100 MO1) for 10 min. The mixture is spun at low 300 g force in ultrafree-MC filter tube where the upper 0.45 urn membrane traps the cells but allows virus to pass through. Cells are lightly washed with 1×PBS, spun again, and then lysed on the membrane for RNA extraction. After RT-PCR from the viral env RNA, the different samples/conditions are subjected to the quantitative OLA to distinguish between the N425 virus and the competitor K425 virus, that was associated with the cells. To our initial surprise, this procedure was quite sensitive and specific considering CXCR4-tropic virus failed remove CCR5-tropic virus pre-incubated with the CD4+/CCR5+ CEM cells 52. However this procedure does require large numbers of cells and virus for efficient detection and to determine binding constants. The K425 virus, as compared to the N425 virus (of the same subtype), will bind with higher efficiency to CD4+ Jurkat cells with or without CCR5. Binding affinity of HIV-1env (+/N425K) can be analyzed using the huCD4+ mouse B cells, isolated from the spleens of our transgenic mice. Higher binding affinity to these cells correlates to a higher titer of CD4i Nab in these transgenic mice, means that a surrogate assay can be used to test the possible immunogenicity of new vaccine designs based on the structural analyses.

Env gp120 Expression and Production

As described, mammalian cells (293 FreeStyle/F cells) in the presence of kifunensine produced gp120 with high-mannose glycans whereas insect cells (Sf9) added mostly paucimannosidic glycans. The gp120 from both of these systems displayed high binding affinity for soluble CD4 and CD4i Abs. In contrast, recombinant gp120 purified from 293F cells in the absence of kifunensine had high-mannose/complex glycans with sialic acid and showed more typical binding affinity to CD4. Thus, we utilize the latter expression system. First, only our N425 and K425 NL4-3 env are be subcloned into the vector pTri-Ex1.1 (Invitrogen) with a C-terminal 6× His tag. Briefly, baculovirus vectors harvested from transfected 293F cells will be used to again infect 293F cells. Glycoproteins is purified from supernatant as described, i.e., by using a combination of lectin followed by nickel (reactive with 6× His tag) affinity chromatography. Briefly, supernatants are initially enriched on the G. nivalis Sepharose column (Vector laboratories), followed by buffer exchange with ProBond native binding buffer (Invitrogen) supplemented with 10 mM imidazole and purification using the Invitrogen ProBond purification system. Eluted glycoproteins will be buffer-exchanged with 20 mM Tris (pH 7.4) and frozen only after determination of >90% pure. It is important to note that this protein will be deglycosylated by PNGaseF or EndoH for crystallization.

Analyses of gp120-CD4 Binding Affinity

We utilize surface plasmon resonance (SPR) based technology to determine biomolecular interactions between sCD4 and rgp120 produced in 293F. Binding assays are performed on a BIA2000 optical biosensor where sCD4 is immobilized on a CM5 sensor chip using amine coupling as described. Prior to all experiments, the binding surfaces are tested with appropriate concentrations of either gp120 or sCD4. The sample solutions are mixed at least 1 h prior to injection. All binding experiments are performed in triplicate and at 25° C. Data points are collected at the highest collection rate (2 Hz). For these binding assays, it is important to adopt the most relevant glycosylation for rgp120. The N425K rap120 will bind to immobilized CD4 with faster on rates and slower off rates than the wt K425 rgp120. A CD4 binding assay based on Biacore platform where the flow-through ligand would be the SHIV vaccine vectors in place of the rgp120 can be utilized.

Immunizing Balb/c Mice and Transgenic Mice with Human CD4+ B Cells, and to Determine if the N425K SHIVenv Vaccine is More Efficient at Eliciting Broadly Neutralizing CD4i Abs The various K425 and N425 env's are cloned into a SHIV attenuated vaccine construct (with a SHIV homolog) for vaccination in mice and macaques. The CD4i Abs will only be selected in our transgenic mice expressing human CD4 on B cells. Sera isolated from mice is tested for Nab against a select panel of viruses. We have also developed a unique screen for mouse B cell hybridomas expressing CD4i Abs.

Although the CD4 binding site in the gp120 C4 domain is relatively well conserved, the CD4i epitopes may be more variable and not all are involved with co-receptor binding. There is limited cross-clade inhibition by Nabs. CD4i Abs may show more crossisolate/clade neutralization when derived from an immunization with a particular N425K SHIVenv vector, i.e., one as compared to another subtype. If each vector derived from a different subtype elicits primarily CD4i Nabs that inhibit HIV-1 isolates of the same subtype within our panels, it can be more effective to combine all five N425K SHIVenv vaccine vector derived from subtypes A, B, C, D, and CRF02_AG. We can also introduce the N425K mutation into our heterogenous SHIVenv constructs for vaccination of macaques. The heterogenous SHIV env constructs, currently being used in macaques, were designed to increase the breath of Ab response. Combining the two approaches can focus response on CD4i epitopes as well as deal with HIV-1 diversity.

Figure 20:
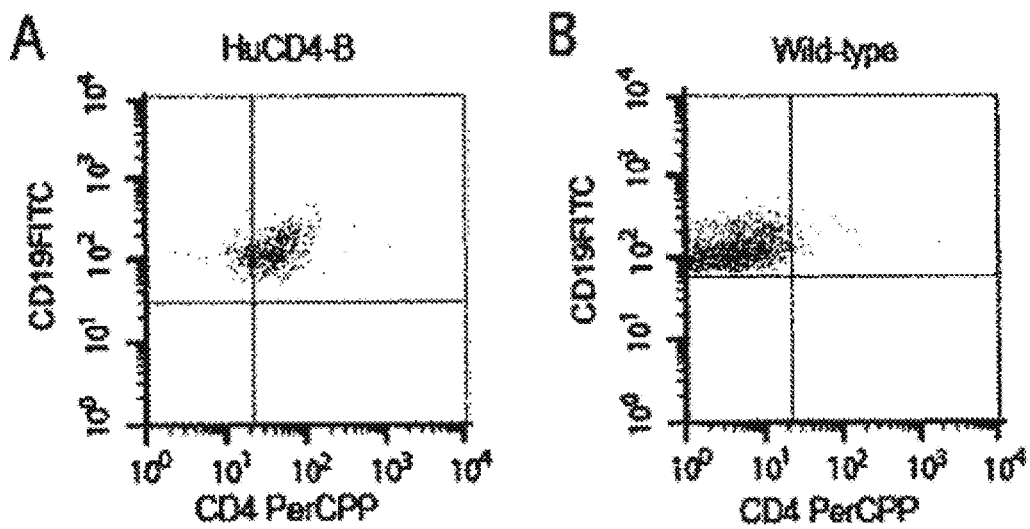
FIG. 20 is a histogram showing flow cytometry on huCD4+ mouse B cells.
Figure 21:
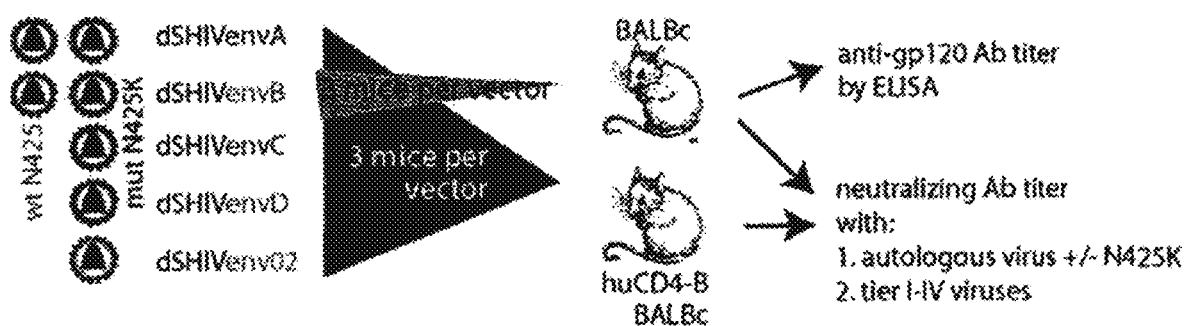
FIG. 21 is schematic drawing showing mouse immunizations in accordance with an aspect of the invention.

Mice are vaccinated with the dSHIVenv vector using a prime-boost strategy with or without adjuvant. Blood is collected to isolate sera for measuring Ab binding and Nab activity. B cells are purified to generate hybridomas and rapidly screened for the production of Nab. Nab activity is then tested against the various wt N425 and N425K strains as well as our panel of tier I-IV viruses.

dSHIVenv vaccine vectors can be constructed as well as replication competent SHIVenv or the HIV-1env chimeric virus to determine sensitivity to Nabs. We can elicit HIV-specific Nabs binding to the CD4i site via vaccination of transgenic mice expressing human CD4. These mice were original constructed for another purpose but we were provided these mice for our studies. FIG. 20 shows the expression of human CD4 on CD19+ immature B cells from the spleens of these transgenic mice (huCD4-B).

Vaccination Procedure

Groups of 3 huCD4-B mice will be primed by the intramuscular route (Quafriceps) with each of dSH-IVEnvA$_{N425K}$, dSHIVEnvA$_{wt(N425)}$, dSHIVEnvB$_{wt(N425)}$, dSH-IVEnvB$_{N425K}$, SHIVEnvB$_{wt(N425)}$, -EnVC$_{N425K}$, -EnvD$_{N425K}$, and -Env02$_{N425K}$ using a total of 21 animals (FIG. 10). Six Balb/c mice will only be immunized with dSHIVEnvB$_{wt(N425)}$ and dSHIVEnvB$_{N425K}$. Immunization dose is $10^7$ TCID$_{50}$ (estimated based on RT activity) per immunization in 100 µl media. All animals are boosted twice every two with weeks. Blood will be sampled from tail veins before immunization, 10 days post-each immunization, and upon sacrifice. Ten days after the final immunization the mice are sacrificed by CO$_2$ gas and the spleen is collected for B cell isolation and generation of hybridomas.

Testing for gp120 Binding and Nabs in the Sera

The majority of our Balb/c mice immunized with two subtype B vaccine constructs will not produce CD4i Nabs but may generate moderate levels of anti-gp120 binding Abs. In contrast, the huCD4-B mice vaccinated with either N425K and wt K425 dSHIV constructs elicit both anti-gp120 binding and Nabs. Based on the increased CD4 binding, higher levels Nab in sera are observed with the N425K versus wt K425 dSHIV. Using the N425K versus wt N425 dSHIVenvB immunized mice, we measure the gp120 binding Ab in the sera using the N425 rgp120- and N425K rgp120-coated plates for ELISAs. Since we only have purified the subtype B rgp120 (+/−N425K), we limit our comparisons anti-rgp120 Abs of N425K versus wt N425 to the dSHIVenvB vaccines in the two types of mice (FIG. 21). If we observe significant differences or just weak trends. We have the option of cloning, expressing, and purifying new rgp120 (+/−N425K) derived from the other subtypes and immunizing with the respective dSHIV constructs. Next, we measure the Nab titer in the sera from all immunized mice by first using the respective/autologous HIV-1 env chimeric virus and the assays previously described. We will then measure cross-clade neutralization in sera from the immunized huCD4-8 mice. Both the N425K and N425 HIV-1env chimeric viruses from the different subtypes are used in the neutralization assays. It is important to note that N425 virus had similar sensitive to the CD4i Ab as other wild type HIV-1 isolates, whereas the N425K virus appeared to be hypersensitive. We produced panel of 20 HIV-1env chimeric viruses that match those in the tier I-IV sensitivity panel and that are derived from subtype A, B, C, and D strains. We test for sera inhibition of this virus panel when sufficient serum volumes are available. As with most broadly neutralizing Abs. our Nabs or sera containing high Nab activity are most inhibitory to the tier I and show the least inhibition of tier IV viruses.

Identifying Monoclonal Ab that Inhibit HIV-1 Via a CD4i Binding Site

The procedure employed for the selection of mouse 8-cell/myeloma hybridomas is described in FIG. 22. At day 10 after the final immunization, spleens are removed, rinsed with 10 ml of M-10 medium, crushed, filtered (70 nm) for cells, washed, and then resuspended in RoboSep buffer to purify 8 cells via negative selection using the EasySep Mouse 8 cell enrichment kit (i.e., removal of non-8 cells expressing CD4, CD8, CD11 b, CD43, CD49b, Ly-6G/C, and TER119). The isolated 8 cells are then be fused with myeloma cells. The post-fusion cells are cultured in HAT and transferred into microtiter plates with peritoneal macrophages 48 hours post-fusion. Only 8 cells that have fused with the myeloma cells will survive in culture when grown in HAT medium. 7 to 21 days post-fusion, hybridoma clones are screened for Nab production.

We employ this hybridoma procedure with 8 cells from mice vaccinated with our heterogenous dSHIVenv construct. Using the dSHIVenvN425K immunized mice, we have two options for selection and to determine the frequency of hybridomas producing CD4i Nabs versus other Nabs. With the first, the supernatant from the clonal hybridomas is added with the autologous NL4-3Env and NL4-3EnvN425K (from the respective Subtype) in the neutralization assay under conditions of low CD4/high CCR5 Affinofile cells. It is expected that: (1) no inhibition of either virus (most likely), (2) equal inhibition of both (likely not a CD41 Ab), and (3) stronger inhibition of NL4-3EnvN425K than the parental. The Nab derived from a specific hybridoma with the greatest differential for inhibition of the N425K vs. wild type dSHIVenv8 can be selected for structural studies. The second method involves the enrichment of only those hybridomas that express Nabs where we would then only have to differentiate between scenarios (2) and (3). The huCD48 cell from the immunized mice are fused with myeloma cells transformed with huCCR5. These HATresistant hybridoma cells would then be added with excess 293T+HSV-TK cells expressing HIV-1 Env via transfection with our pRECnfCenvN425K or pRECnfCenvwt constructs. We have confirmed that these CD4+/CCR5+ hybridomas fuse with the 293T+TK+Env cells. If gancyclovir is added, all the free 293T+TK+Env cells and fused cells die due to the synthesis of the toxic GCV-TP via HSV TK (thymidine kinase). The hybridomas can survive and propagate if they express a Nab to block this Env-mediated fusion. It is important to note that although cell fusion via Env-CD4/CCR5 interaction is similar to the virus entry event, Nabs are often less effective in blocking cell fusion possible due to the increased steric hindrance between the two cell membranes.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A vaccine for HIV-1 comprising:

a vector, the vector including an HIV-1 backbone coding sequence;

a replication defective polynucleotide encoding a gp120 HIV-1 envelope protein having an N425K mutation, based on HBX2 reference virus numbering, wherein the gp120 HIV-1 envelope protein having an N425K mutation binds to CD4; and a pharmaceutically acceptable carrier.

2. The vaccine of claim 1, wherein the gp120 HIV-1 envelope protein including an N425K mutation induces an immune response to HIV-1 when administered to a subject.

3. The vaccine of claim 2, the immune response comprising the generation of broadly neutralizing induced CD4 (CD4i) HIV-1 antibodies directed to a CD4 coreceptor binding site of HIV-1.

4. The vaccine of claim 1, the vector comprising a NL4-3 backbone HIV-1 vector.

5. The vaccine of claim 1, the vector comprising a SHIV vector.

6. The vaccine of claim 1, wherein the replication defective polynucleotide encoding a gp120 HIV-1 envelope protein having an N425K mutation is prepared from an HIV-1 virus having the mutation.

7. A method of producing broadly neutralizing CD4i HIV-1 antibodies in a host subject, the method comprising:

administering to the host subject a vaccine for HIV-1, the vaccine including a vector, the vector including an HIV-1 backbone coding sequence and a replication defective polynucleotide encoding a gp120 HIV-1 envelope protein having an N425K mutation, wherein the gp120 HIV-1 envelope protein having an N425K mutation binds to CD4, and a pharmaceutically acceptable carrier;

obtaining a biological sample from the host subject, the sample including broadly neutralizing CD4i antibodies directed to a CD4 coreceptor biding site of HIV-1 generated by the host in response to the vaccine; and isolating the broadly neutralizing CD4i antibodies from the sample.

8. The method of claim 7, wherein the host subject is a CD4 human CD4+B cell transgenic mouse.

9. The method of claim 7, the biological sample comprising a blood sample.

* * * * *